(12) United States Patent
Dowling et al.

(10) Patent No.: US 11,191,781 B2
(45) Date of Patent: Dec. 7, 2021

(54) COMPOSITIONS AND METHODS OF TREATING DRY EYE SYNDROME AND OTHER TRAUMATIZED NON-KERATINIZED EPITHELIAL SURFACES

(71) Applicant: Eye Care International, LLC, Lloyd Neck, NY (US)

(72) Inventors: Matthew B. Dowling, Olney, MD (US); Steven E. Lazar, Flemington, NJ (US); Helga M. Gentile, Lloyd Neck, NY (US)

(73) Assignee: Eye Care International, LLC, Lloyd Neck, NY (US)

( * ) Notice: Subject to any disclaimer, the term of this patent is extended or adjusted under 35 U.S.C. 154(b) by 378 days.

(21) Appl. No.: 16/309,810

(22) PCT Filed: Jun. 16, 2017

(86) PCT No.: PCT/US2017/037954
§ 371 (c)(1),
(2) Date: Dec. 13, 2018

(87) PCT Pub. No.: WO2017/218942
PCT Pub. Date: Dec. 21, 2017

(65) Prior Publication Data
US 2019/0175647 A1 Jun. 13, 2019

Related U.S. Application Data

(60) Provisional application No. 62/350,772, filed on Jun. 16, 2016.

(51) Int. Cl.
| | |
|---|---|
| *A61K 35/16* | (2015.01) |
| *A61K 31/722* | (2006.01) |
| *A61P 27/04* | (2006.01) |
| *A61K 9/00* | (2006.01) |
| *A61K 9/19* | (2006.01) |
| *A61K 47/36* | (2006.01) |
| *A61B 5/00* | (2006.01) |
| *A61P 27/02* | (2006.01) |
| *A61K 35/51* | (2015.01) |
| *A61K 47/26* | (2006.01) |

(52) U.S. Cl.
CPC ............ *A61K 35/16* (2013.01); *A61B 5/4875* (2013.01); *A61K 9/0048* (2013.01); *A61K 9/19* (2013.01); *A61K 31/722* (2013.01); *A61K 35/51* (2013.01); *A61K 47/26* (2013.01); *A61K 47/36* (2013.01); *A61P 27/02* (2018.01); *A61P 27/04* (2018.01)

(58) Field of Classification Search
CPC .................... A61K 9/0048; A61K 9/19; A61K 31/715–736; A61K 35/16; A61K 35/51; A61K 47/26; A61K 47/36; A61K 47/51; A61K 47/55; A61K 47/56–61
See application file for complete search history.

(56) References Cited

U.S. PATENT DOCUMENTS

| | | | |
|---|---|---|---|
| 8,017,157 B2 | 9/2011 | Yoo et al. | |
| 8,932,560 B2 | 1/2015 | Dowling et al. | |
| 9,616,088 B2 | 4/2017 | Diehn et al. | |
| 2009/0035289 A1* | 2/2009 | Wagner | A61K 35/16 424/93.72 |
| 2009/0170059 A1 | 7/2009 | Klingemann | |
| 2009/0223080 A1 | 9/2009 | McCarthy | |
| 2011/0282325 A1 | 11/2011 | Gregory | |
| 2014/0319141 A1 | 10/2014 | Stratis | |
| 2016/0206777 A1 | 7/2016 | Dowling et al. | |

FOREIGN PATENT DOCUMENTS

| | | |
|---|---|---|
| JP | 2010522176 A | 7/2010 |
| WO | 99/01498 A1 | 1/1999 |
| WO | WO-2000/030609 | 6/2000 |
| WO | 2008/115548 A2 | 9/2008 |
| WO | WO-2015/048774 A2 | 4/2015 |
| WO | WO-2015/123778 A1 | 8/2015 |
| WO | 2017/218942 A1 | 12/2017 |

OTHER PUBLICATIONS

Lee, J. et al "Vesicle-biopolymer gels . . . " Langmuir, vol. 21, No. 1, pp. 26-33. (Year: 2005).*
Jang, C. et al "Effect of umbilical cord serum . . . " Int. J. Ped. Otorhinolaryngol., vol. 78, issue 7, pp. 1061-1065. (Year: 2014).*
Thomas, M. et al "A method ofr the cryopreservation of red blood cells . . . " Transfus. Sci., vol. 17, issue 3, pp. 385-396. (Year: 1996).*

(Continued)

*Primary Examiner* — Leigh C Maier
(74) *Attorney, Agent, or Firm* — Muriel Liberto, Esq.; Mintz Levin Cohn Ferris Glovsky and Popeo, P.C.

(57) ABSTRACT

The present disclosure relates to a composition including non-autologous plasma or serum and a polymer; method of treating ophthalmic diseases (e.g., dry eye syndrome) or moisturizing and/or repairing non-keratinized surfaces including non-healing wounds with a composition including non-autologous plasma or serum and a polymer; and a therapeutic agent delivery device for delivery of the composition to the eye or a non-keratinized surface of a subject.

15 Claims, 3 Drawing Sheets

(56) References Cited

OTHER PUBLICATIONS

Kojima, T. et al "Autologous serum eye drops . . . " Cornea, vol. 27, No. 8, suppl. 1, pp S25-S30. (Year: 2008).*
Aragona, P. et al "Sodium hyaluronate eye drops of different osmolarity . . . " Br. J. Ophthalmol., vol. 86, pp. 879-884. (Year: 2002).*
Alio J., et al., (Jun. 2012). "The role of "eye platelet rich plasma" (E-Prp) for wound healing ophthalmology." Current Pharmaceutical Biotechnology 13(7):1257-1265.
Bakaltcheva I., et al., (May 7, 2007). "Freeze-dried whole plasma: Evaluating sucrose, trehalose, sorbitol, mannitol and glycine as stabilizers." Thrombosis Research 120(1):105-116.
Kutlu B., et al., (Jan. 15, 2013). "Platelet-rich plasma-loaded chitosan scaffolds: preparation and growth factor release kinetics." Journal of Biomedical Materials Research Part B: Applied Biomaterials 101B(1):28-35.
Poon A., et al. (Oct. 1, 2001). "Autologous serum eyedrops for dry eyes and epithelial defects: clinical and in vitro toxicity studies." British Journal of Ophthalmology 85(10):1188-1197.
Yoon K-C., et al. (Jun. 26, 2007). "Comparison of autologous serum and umbilical cord serum eye drops for dry eye syndrome." American Journal of Ophthalmology 144(1):86-92.
Extended European Search Report dated Feb. 3, 2020 for European Application No. 17814202.2, filed Jun. 16, 2017.
International Search Report dated Sep. 12, 2017 for International Application No. PCT/US2017/037954, filed Jun. 16, 2017.

\* cited by examiner

COMPOSITIONS AND METHODS OF TREATING DRY EYE SYNDROME AND OTHER TRAUMATIZED NON-KERATINIZED EPITHELIAL SURFACES

CROSS-REFERENCE TO RELATED APPLICATIONS

This application is a national stage entry, filed under 35 U.S.C. § 371, of International Application No. PCT/US2017/037954, filed on Jun. 16, 2017, which claims the benefit of priority under 35 U.S.C. § 119(e) to U.S. Provisional Patent Application No. 62/350,772, filed Jun. 16, 2016, which is hereby incorporated by reference in its entirety.

BACKGROUND OF THE DISCLOSURE

Non-keratinized epithelial surfaces are found throughout much of the body, except the limbs, and with the exception of the eye-ball, are predominantly out of sight. Lubrication is continually bathing non-keratinized epithelial surfaces that can range from a thin watery aqueous solution to a thick, viscous fluid called mucus. Lubrication is secreted by exocrine glands that also range from unicellular glands known as goblet cells that secrete via an apocrine method, budding off their secretions in membrane-bound vesicles, to complex multicellular glands that discharge secretions via a duct. Non-keratinized epithelial lubrication contains glycoproteins, proteoglycans, peptides, and enzymes that both promote and protect the health of epithelial cells. Not only does the lubrication protect the non-keratinized epithelial from mechanical irritation from frictional trauma, it also provides antimicrobial properties, preventing invasion from infectious organisms, a constant threat to these exposed areas. Non-keratinized epithelial surfaces form the lining of the cornea, conjunctiva, mouth, pharynx, esophagus, vocal cords, vagina, and cervix and play a vital role in the gastrointestinal, respiratory, and urogenital tracts.

These tissues are all sites of communication, where material and information are passed between the body and its environment. Because of their physiological functions of sensory activity (eyes, nose, mouth, and throat), gas exchange (lungs), food absorption (gut), and reproduction (uterus, vagina, and breast), the non-keratinized epithelial surfaces are by necessity dynamic, thin, permeable barriers to the interior of the body. These properties make these tissues particularly vulnerable to subversion and breach by pathogens. This fragility, combined with the vital functions of non-keratinized epithelial surfaces, has driven the evolution of specialized mechanisms for their defense.

Dry eye syndrome is a large and growing problem and is very common with an estimated 25% of patients in general ophthalmology or optometry clinics reporting symptoms of dry eye syndrome. It has multiple causes that result in an unstable tear film and rapid tear film breakup time. Dry eye syndrome is a multifactorial disease of the tears and ocular surface that results in symptoms of blurry vision and discomfort including foreign body sensation, irritation, burning, and light sensitivity. Dry eye and tear film instability can damage the ocular surface. It is accompanied by increased osmolarity of the tear film and inflammation of the ocular surface.

Currently, there is no cure for dry eye syndrome and common treatments are targeted to merely manage the symptoms. The mainstay of conventional therapy is the application of artificial tears that increase moisture on the ocular surface, and provide additional lubrication. A variety of artificial tear formulations differ from each other in their electrolyte composition, osmolarity, viscosity, presence or absence of preservatives, and compatible solutes. However, frequent application of artificial tears containing preservatives to prevent contamination has been found to include both toxic and allergic reactions, especially in patients with sensitive eyes.

There is currently a need for an ophthalmic composition for the treatment of dry eye syndrome. Among many challenges in developing dry eye therapy is the inability to deliver a composition that is retained on the eye surface for a prolonged period. Topical administration, mostly in the form of eye drops, is usually employed to treat eye anterior segment diseases. For most of the topically applied drugs, the site of action is usually different layers of the cornea, conjunctiva, sclera, and the other tissues of the anterior segment such as the iris and ciliary body (anterior uvea). Upon administration, precorneal factors and anatomical barriers negatively affect the bioavailability of topical formulations. Precorneal factors include solution drainage, blinking, tear film, tear turn over, and induced lacrimation. Tear film displays a rapid restoration time of 2-3 min, and most of the topically administered solutions are washed away within just 15-30 s after instillation. Considering all the precorneal factors, contact time with the absorptive membranes is lower, which is considered to be the primary reason for less than 5% of the applied dose reaching the intraocular tissues. Precorneal factors, however, are not a major obstacle in treating dry eye syndrome.

Various layers of cornea, conjunctiva, and sclera also play an important role in drug permeation. The cornea, the anterior most layer of the eye, is a mechanical barrier which limits the entry of exogenous substances into the eye and protects the ocular tissues. It can be mainly divided into the epithelium, stroma, and endothelium. Each layer offers a different polarity and a potential rate-limiting structure for drug permeation. The corneal epithelium is lipoidal in nature which contains 90% of the total cells in the cornea and poses a significant resistance for permeation of topically administered hydrophilic drugs. Furthermore, superficial corneal epithelial cells are joined to one another by desmosomes and are surrounded by ribbon-like tight junctional complexes (zonula occludens). Presence of these tight junctional complexes retards paracellular drug permeation from the tear film into intercellular spaces of the epithelium as well as inner layers of the cornea.

The stroma, which comprises 90% of the corneal thickness, is made up of an extracellular matrix and consists of a lamellar arrangement of collagen fibrils. The highly dense structure of the stroma poses a significant barrier to permeation of lipophilic drug molecules. Endothelium is the innermost monolayer of hexagonal-shaped cells. Even though endothelium is a separating barrier between the stroma and aqueous humor, it helps maintain corneal transparency due to its selective carrier-mediated transport and secretory function. Furthermore, the corneal endothelial junctions are leaky and facilitate the passage of macromolecules between the aqueous humor and stroma. Thus, corneal layers, particularly the epithelium and stroma, are considered as major barriers for ocular drug delivery. The permeant should have an amphipathic nature in order to permeate through these layers.

Compared to the cornea, conjunctival drug absorption is considered to be nonproductive due to the presence of conjunctival blood capillaries and lymphatics, which can cause significant drug loss into the systemic circulation thereby lowering ocular bioavailability. Conjunctival epithelial tight junctions can further retard passive movement of hydrophilic molecules. The sclera, which is continuous with the cornea originates from the limbus and extends posteriorly throughout the remainder of the globe. The sclera mainly consists of collagen fibers and proteoglycans embedded in an extracellular matrix. Permeability through the sclera is considered to be comparable to that of the corneal stroma. The permeability of drug molecules across the sclera is inversely proportional to the molecular radius. Dextrans with linear structures were less permeable as compared to globular proteins. Furthermore, the charge of the drug molecule also affects its permeability across the sclera. Positively charged molecules exhibit poor permeability presumably due to their binding to the negatively charged proteoglycan matrix.

For treating dry eye syndrome a composition is needed that would have maximal contact time with the absorptive membrane and reduced permeability across the various layers of the cornea, conjunctiva, and sclera. Described herein are compositions for effective treatment of dry eye syndrome and ameliorating its symptoms.

SUMMARY OF THE DISCLOSURE

The current disclosure provides, inter alia, a freeze-dried composition including non-autologous plasma or serum and a polymer; a method of treating ophthalmic diseases (e.g., dry eye syndrome), the method including applying the re-constituted freeze-dried composition; and an ophthalmic therapeutic agent delivery device (100) including two chambers, wherein the first chamber (101) configured for storing a freeze-dried ophthalmic composition including of non-autologous plasma or serum, and a and a second chamber (102) including a reconstitution fluid. In one aspect the present disclosure provides compositions for moisturizing and/or repairing non-keratinized epithelial surfaces in or on the body of a subject. Examples include treatment of dry mouth syndrome, vaginal dryness, diabetic ulcers and other chronic wounds. In embodiments, a freeze-dried composition for treating dry eye syndrome or for moisturizing and/or repairing non-keratinized epithelial surfaces is disclosed, where the composition includes non-autologous plasma or serum, and a polymer having a molecular weight of 100 to 1200 kDA, or derivatives thereof. In embodiments the non-autologous plasma or serum of the freeze-dried composition may be of umbilical cord plasma or serum.

In embodiments, the disclosure provides a freeze-dried composition comprising non-autologous plasma or serum and a polymer that is a biopolymer, preferably a polysaccharide having a molecular weight of 100 to 1200 kDa, preferably from 100 to 400 kDa, or a polysaccharide having a molecular weight of 100, 250, or 400 kDa, wherein the polysaccharide is chitosan, or a hydrophobically modified chitosan. In embodiments, the freeze-dried composition comprises serum or plasma in an amount as described infra. In embodiments, the composition is biodegradable and biocompatible. In embodiments, the freeze-dried composition is in the form of a cohesive solid state material, such as a disc, wafer, lens, pessary, wound dressing, or denture. In embodiments, the freeze-dried composition in the form of a solid material is further combined with a sufficient amount of an aqueous liquid (e.g., a reconstitution fluid). In embodiments, liquid serum or plasma may be used as the reconstitution fluid, either alone or diluted with an appropriate aqueous carrier, for example water or saline. In embodiments, the aqueous liquid is any solvent described herein. In exemplary embodiments, water or a saline solution may be used, any additives may be included (e.g., glycine or ascorbic acid). In embodiments, the disclosure provides a freeze-dried composition in the form of a cohesive solid state material along with a reconstitution fluid which when mixed with the cohesive solid state material forms a cohesive sponge-like material. In another embodiment, the freeze-dried composition is in the form of a dry powder which can be formulated into a suitable dosage form for topical application to a non-keratinized epithelial surface, such as the surface of the eye, mouth, or vagina, or the surface of an external wound. Such powder compositions may be formulated, for example, as a liquid, gel, or ointment. Preferably, the compositions are sterile.

The freeze-dried plasma or serum and polysaccharide based compositions described here have numerous advantageous properties. For example, the compositions are biodegradable and biocompatible with animal tissues, especially with non-keratinized epithelial surfaces, such as the surface of the eye, mouth, or vagina, or the surface of an external wound. In embodiments, the compositions contain biologically active plasma or serum derived proteins whose dissolution from the site of application is slowed by the matrix-like structure of the composition. Accordingly, the disclosure provides methods of promoting the healing of a damaged or traumatized non-keratinized epithelial surface, including the surface of an external wound, by applying an amount of a composition described here to the surface.

In embodiments, the composition forms a matrix-like structure that enables slow release of the biologically active components present in the plasma or serum after application to a non-keratinized epithelial surface, such as the eye for the treatment of ocular diseases and disorders including, but not limited to, dry eye syndrome. In other aspects, the freeze-dried composition described herein also promotes health of the underlying corneal epithelium, as evidenced for example by the uptake of Rose Bengal dye according to standard assays for the detection of corneal epithelial damage, e.g., in dry eye patients. In embodiments, the compositions described here also improve tear break up time, as measured by standard assays.

In embodiments the polymer of the freeze-dried composition may be a linear biopolymer. In some aspects, the polymer may be modified to be soluble in an aqueous solution. In embodiments, the polymer of the freeze-dried composition may be a basic biopolymer with pH more than 7.0. In some embodiments, the polymer may be cationic, anionic or zwitterionic and may be selected from chitosans, alginates, gelatins, and a combination thereof. In embodiments, the chitosan may be selected from hydrophobically-modified chitosan, carboxymethyl chitosan, succinyl chitosan, glycol chitosan, thiolated chitosan and a combination thereof.

In embodiments, the freeze-dried composition may further include an additive. In embodiments, the additive may be selected from chitosan, alginate, gelatin, hyaluronic acid, gellan gum, dextran, polyethylene glycol, polyethylene oxide, glucose, glucosamine, sodium chloride, polylactic acid, polylactic-co-glycolic acid and glycerol.

In embodiments, the non-autologous plasma or serum in the freeze-dried ophthalmic composition may be at a concentration of about 0.005 to 100% by weight/vol. (w/v) of the composition.

In embodiments, the composition is reconstituted with a reconstitution fluid. In embodiments, the reconstitution fluid may further include an additive, wherein the additive is selected from ascorbic acid, glycine, and combination thereof. The reconstituted composition may have a final pH of about 7.4.

In embodiments, the composition comprises non-autologous serum, and a polymer having a molecular weight of 100 to 1200 kDa. Alternatively, the composition is a freeze-dried composition comprising plasma or serum and a polysaccharide having a molecular weight of from 100 to 400 kDa. In embodiments, the polysaccharide is selected from the group consisting of chitosan, cellulose, dextrin, pectin, alginic acid, agar, agarose, carragenas, and derivatives thereof. In other embodiments, the polysaccharide is chitosan, or a hydrophobically modified chitosan.

In embodiments, the freeze-dried composition described here is in the form of a cohesive solid state material having a defined shape. In embodiments, the solid state material is sufficiently cohesive that it does not crack under low or moderate pressure. In embodiments, the freeze-dried composition in the form of a cohesive solid state material having a defined shape comprises serum or plasma and chitosan, preferably a hydrophobically modified chitosan as described infra. In embodiments, the chitosan is hydrophobically modified with palmitic anhydride, as described infra. In embodiments, the cohesive solid state material is in the form of a disc, wafer, lens, pessary, wound dressing, or denture. In embodiments where a more cohesive material is desired, the freeze-dried composition comprises serum and chitosan, or a hydrophobically modified chitosan as described infra.

In embodiments, the freeze-dried composition described herein is in the form of a dry powder. In embodiments, the freeze-dried composition in the form of a dry powder comprises serum or plasma and chitosan, preferably a hydrophobically modified chitosan as described infra. In embodiments, the chitosan is hydrophobically modified with palmitic anhydride, as described infra. In embodiments, the freeze-dried composition comprises serum and chitosan, or a hydrophobically modified chitosan as described infra.

In accordance with any of the solid-state embodiments of the freeze-dried compositions described here, the amount of serum or plasma components in the dry composition is from about 50-90 weight percent (wt %) based on the total dry weight of the composition, and the amount of polysaccharide is from about 10-40 wt %. In embodiments, the freeze-dried composition contains from about 60-80 wt % of serum or plasma components and from about 20-40 wt % polysaccharide, or from about 70-80 wt % of serum or plasma components and from about 20-30 wt % polysaccharide.

In embodiments, the disclosure provides a freeze-dried composition comprising plasma or serum and a polysaccharide selected from chitosan, a hydrophobically modified chitosan, sucrose, or trehalose, wherein the composition comprises from about 60-90 wt % of the plasma or serum components and from about 10-40 wt % of the polysaccharide.

In accordance with any of the solid-state embodiments of the freeze-dried compositions described above, the composition may be formulated as a pharmaceutical composition, which may take the form of a liquid, suspension, ointment, or gel, depending on the carriers and, one or more optional excipients, included in the formulation. Accordingly, the disclosure provides pharmaceutical compositions comprising the freeze-dried compositions described here, which further comprise a carrier and one or more optional excipients. In embodiments, the carrier is an aqueous solution, for example water or buffered saline. In embodiments, the one or more optional excipients may include, for example, ethanol, a polyol, a surfactant, or a carbohydrate. In embodiments, the one or more optional excipients may be selected from sucrose and trehalose. In embodiments, the pharmaceutical composition is sterile.

Provided herein is a method for treating dry eye syndrome or a method of moisturizing and/or repairing non-keratinized surfaces (e.g., dry mouth syndrome, vaginal dryness, diabetic ulcers and other chronic wounds), in a subject in need thereof including: administering a composition including non-autologous plasma or serum, and a polymer having a molecular weight of 100 to 1200 kDA, or derivatives thereof, and the non-autologous plasma or serum is present in the composition an amount effective to treat dry eye syndrome in the eye or moisturizing and/or repairing non-keratinized surfaces (e.g., dry mouth syndrome, vaginal dryness, diabetic ulcers and other chronic wounds), respectively, of the subject. In embodiments, the non-autologous plasma or serum has been lyophilized and reconstituted.

Also provided herein are methods for treating a non-keratinized epithelial surface of a subject in need of such treatment, the method comprising applying to the surface a composition comprising non-autologous plasma or serum, and a polymer having a molecular weight of 100 to 1200 kDA, or derivatives thereof, wherein the non-autologous plasma or serum is present in the composition in an amount effective to treat the non-keratinized epithelial surface of the subject. In embodiments, the non-keratinized epithelial surface is selected from an ocular surface, an oral surface, a vaginal surface, and the surface of an external wound.

In embodiments the plasma or serum is of umbilical cord plasma or serum. In embodiments, the polymer is a linear biopolymer. In embodiments, the polymer is modified to be soluble in an aqueous solution. In embodiments, the polymer is a basic biopolymer with pH more than 7.0. In embodiments, the polymer is polycationic or polyanionic.

In embodiments, the polymer is a chitosan, alginate, gelatin, or any combination(s) thereof. In embodiments, the polymer is a chitosan. In embodiments, the chitosan is selected from carboxymethyl chitosan, succinyl chitosan, glycol chitosan, thiolated chitosan and a combination thereof. In embodiments, the chitosan is a hydrophobically modified chitosan. In embodiments, the hydrophobically modified chitosan is selected from chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, and chitosan glycolate. In embodiments, the hydrophobic substituents of the hydrophobically modified chitosan are provided by palmitic anhydride. In accordance with these embodiments, the amount of the polymer in the freeze-dried composition is from about 10-50 wt %, or from about 20-40 wt %, or from about 20-30 wt %, based on the total dry weight of the composition. In accordance with these embodiments, the serum or plasma components will make up the bulk of the remainder, or the entirety of the remainder of the dry weight. In embodiments, the amount of serum or plasma components in the composition is from about 50-90 wt %, or from about 60-80 wt %, or from about 70-80 wt %.

In embodiments, the reconstituted composition is formulated as a solution, suspension, semi-liquid, semi-solid gel, gel, emulsion, ointment, or cream. In embodiments, the reconstituted composition is administered topically. In other embodiments, the reconstituted composition is administered in the form of eye drops. In other embodiments, the reconstituted composition may be administered orally for dry mouth syndrome. In embodiments, the oral administration for dry mouth syndrome may be via a mouthwash, a mouth rinse, an oral rinse, a mouth bath, and the like. In embodiments, administration to the cervical and/or vaginal mucosa may be via a solution, gel, suspension, cream, ointment, foam, pessary, or tablet.

In other embodiments, the reconstituted composition may be administered to the cervical and/or vaginal mucosa of a subject. In embodiments, the cervical and/or vaginal mucosa administration may be via a solution, gel, suspension, cream, ointment, foam, pessary, or tablet. Alternatively, the reconstituted composition may be administered by continuous release from a vaginal ring and the like.

In embodiments, the reconstituted composition may be administered to diabetic ulcers and other chronic wounds of a subject. In embodiments, administration to diabetic ulcers and other chronic wounds may be administered topically or orally. In embodiments, topical administration may include a solution, suspension, semi-liquid, semi-solid gel, gel, emulsion, ointment, or cream. In embodiments, oral administration may include a tablet.

In embodiments, the non-autologous plasma or serum in the composition is at a concentration of about 0.005 to 100% (w/v) of the composition. In embodiments the non-autologous plasma or serum in the composition is at a concentration of about 75% (w/v) to 90% (w/v) and 10-30%. In embodiments, the non-autologous plasma or serum in the composition is at a concentration of about 40% to 60% (w/v) of the composition.

In embodiments, the disclosure provides a freeze-dried composition comprising plasma or serum and a polysaccharide, preferably chitosan or a hydrophobically modified chitosan, for use in methods for treating a non-keratinized epithelial surface, including an external wound, of a subject in need of such treatment. In embodiments, the polysaccharide is a chitosan having a molecular weight of from 100 to 400 kDa. In embodiments, the polysaccharide is a hydrophobically modified chitosan in which the hydrophobic substituent is provided by palmitic anhydride.

In embodiments, compositions including any of the compositions described for use in a subject in need of such treatment. In embodiments, the disclosure provides a freeze-dried composition comprising plasma or serum and a polysaccharide, preferably chitosan or a hydrophobically modified chitosan, for use in methods for treating dry eye syndrome in a subject in need of such treatment. In embodiments, the polysaccharide is a chitosan having a molecular weight of from 100 to 400 kDa. In embodiments, the polysaccharide is a hydrophobically modified chitosan in which the hydrophobic substituent is provided by palmitic anhydride.

Also provided herein is a therapeutic agent delivery device (100) including two chambers (101, 102), where the first chamber (101) is configured for storing a freeze-dried composition including of non-autologous plasma or serum, and a polymer having a molecular weight of 100 to 1200 kDA, or derivatives thereof, and a second chamber (102) is configured for storing a reconstitution fluid.

In embodiments, the non-autologous plasma or serum is of umbilical cord plasma or serum. In embodiments, the polymer is a linear biopolymer. In embodiments, the polymer is modified to be soluble in an aqueous solution. In embodiments, the polymer is a basic biopolymer with pH more than 7.0. In embodiments the polymer is polycationic. In embodiments, the polymer is selected from the chitosans, alginates, gelatins, and a combination thereof. In embodiments, the linear biopolymer is a chitosan. In embodiments, the chitosan is selected from carboxymethyl chitosan, succinyl chitosan, glycol chitosan, thiolated chitosan and a combination thereof. In embodiments, freeze-dried ophthalmic composition is reconstituted with the reconstitution fluid such that the final pH is about 7.4.

In embodiments the two chambers (101, 102) of the therapeutic agent delivery device (100) are disrupted electromechanically or mechanically, thereby allowing mixing of the freeze-dried composition and the reconstitution fluid, thereby generating a reconstituted serum or plasma formulation.

In embodiments, the therapeutic agent delivery device (100) of the present disclosure includes a freeze-dried composition in the first chamber (101) and a reconstitution fluid in the second chamber (102), and upon reconstitution, the reconstituted composition is delivered to a subject.

In embodiments, the therapeutic agent delivery device (100) of the present disclosure includes the reconstituted composition which is for treating dry eye syndrome, or moisturizing and/or repairing a non-keratinized surface.

Other features and advantages of the disclosure will be apparent from the following detailed description and claims.

Unless noted to the contrary, all publications, references, patents and/or patent applications reference herein are hereby incorporated by reference in their entirety for all purposes.

DETAILED DESCRIPTION OF THE DISCLOSURE

Figure 1:
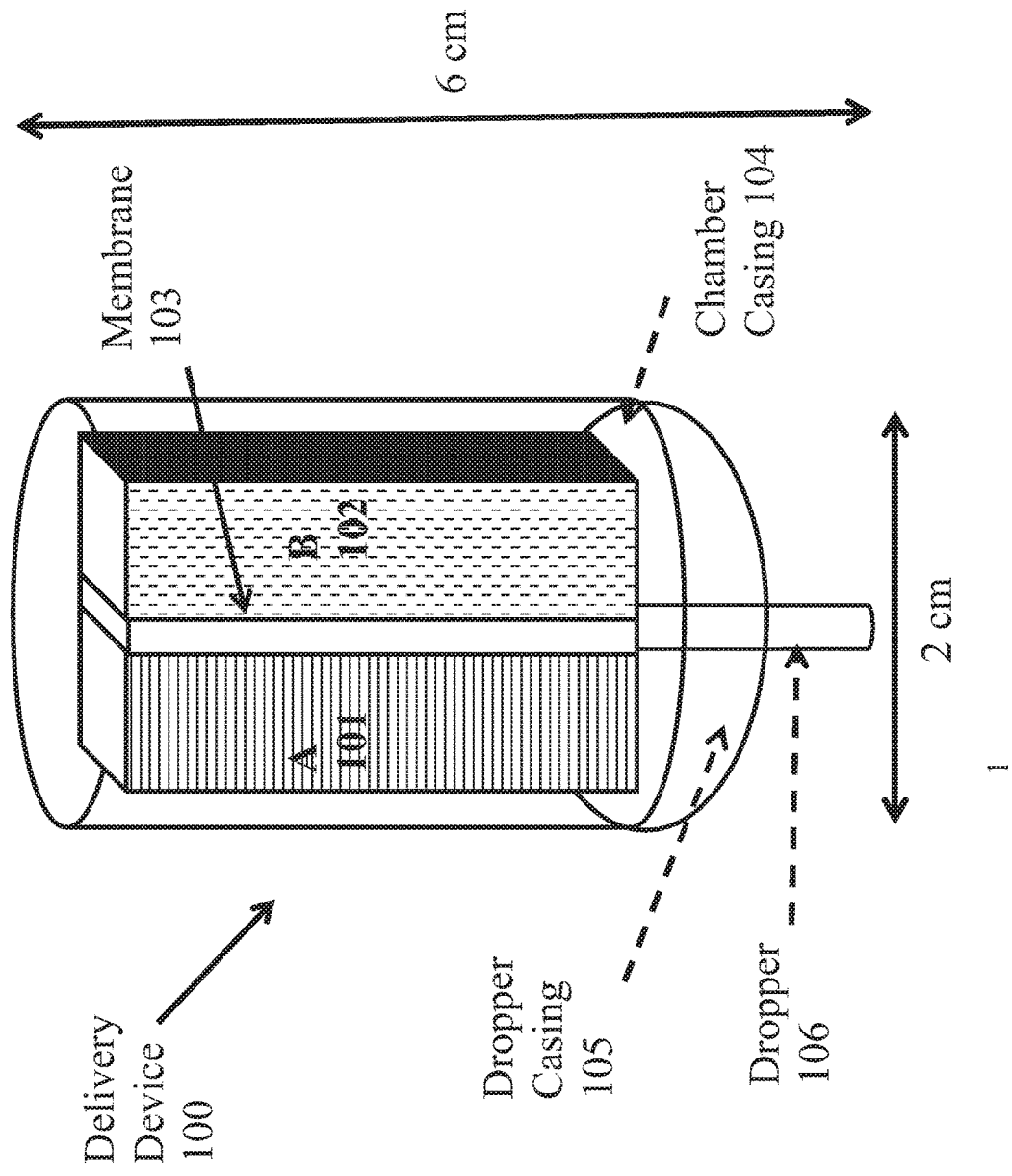
FIG. 1 shows a schematic of a therapeutic agent delivery device (100)

Provided herein, inter alia, is a freeze-dried ophthalmic composition including non-autologous plasma or serum and a polymer; a method of treating ophthalmic diseases (e.g., dry eye syndrome) of a subject in need thereof, the method including applying the reconstituted freeze-dried ophthalmic composition (e.g., non-autologous plasma or serum and a polymer); and a delivery device (100) including the freeze-dried ophthalmic composition and a reconstitution fluid.

Definitions

The following definitions are included for the purpose of understanding the present subject matter and for constructing the appended patent claims. Abbreviations used herein have their conventional meaning within the chemical and biological arts.

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et. al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about. About with respect to concentration range of the compositions of the current disclosure also refers to any variation of a stated amount or range which would be an effective amount or range.

As used herein, "additive" can include any additional components that may be added to the composition as described herein. The additive may be added prior to freeze-drying or prior to reconstitution. One or more additives may be added to the composition. The additive may include components that have been classified by the FDA, and in embodiments may be classified as Ophthalmic Drug Products for Over-The-Counter Human Use [Title 21, Volume 5]. Exemplary additives may include astringents, buffering agents, demulcents, emollients, eyewash, eye lotion, irrigating solutions, hypertonic agents, isotonic agents and vasoconstrictors. Additives in the current disclosure may be used in any suitable amount.

As used herein, the term "administering" means oral administration, administration as a suppository, topical contact (e.g., eye drops or a spray), intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, cervical, rectal, or transdermal). Parenteral administration includes, e.g., intravenous, intramuscular, intra-arteriole, intradermal, subcutaneous, intraperitoneal, and intraventricular.

Administering may further include via oral administration (e.g., for the treatment of dry mouth syndrome). In some examples, administration orally may include a mouthwash, a mouth rinse, an oral rinse, a mouth bath, and the like. Cervical and/or vaginal mucosa administration may be via a solution, a gel, a suspension, a cream, an ointment, a foam, a pessary, or a tablet. In one aspect, the reconstituted composition may be administered to the cervical and/or vaginal mucosa of a subject. The cervical and/or vaginal mucosa administration may be via a solution, gel, suspension, cream, ointment, foam, pessary, or tablet. Alternatively, the reconstituted composition may be administered by continuous release from a vaginal ring and the like. Administration may include administration to diabetic ulcers and other chronic wounds of a subject. Administration to diabetic ulcers and other chronic wounds may be administered topically or orally. Topical administration may include a solution, suspension, semi-liquid, semi-solid gel, gel, emulsion, ointment, or cream. Oral administration may include a tablet.

As used herein, the term "autologous" refers denoting, relating to, or involving tissues or cells that are from one's own sample (i.e., a patient's own blood or blood components). Autologous plasma or serum is usually not readily available from a blood bank or a central repository unless it has been previously donated by the recipient.

"Biopolymers" as used herein may refer to polymers that are produced by living organisms; they are "polymeric biomolecules." Since they are polymers, biopolymers contain repeat monomeric units that are covalently bonded to form larger structures (i.e., linear biopolymers). Exemplary biopolymers may include cellulose, starch, lignin, chitin, and various polysaccharides. These materials and their derivatives offer a wide range of properties and applications. Natural polymers tend to be readily biodegradable, although the rate of degradation is generally inversely proportional to the extent of chemical modification.

"Chitosan" as used herein refers to the principle derivative of chitin, is formed from chitin by deacetylation in the presence of alkali. Chitin, a polymer of N-acetylglucosamine, is a cellulose-like biopolymer that is the main component of crustaceans (e.g. shrimp, crab, lobster) and is also present in the exoskeleton and the cell wall of fungi, insects and yeast. Chitosan is a linear polysaccharide composed of $(1\rightarrow 4)$-2-acetamido-2-deoxy-b-D-glucan (N-acetyl D-glucosamine) and $(1\rightarrow 4)$-2-amino-2-deoxyb-D-glucan (D-glucosamine) units. Chitosan has numerous biological properties, including antimicrobial activity, hemostatic activity, and acceleration of wound healing, tissue-engineering scaffolds, drug delivery, and antitumor activity. Chitosan's inherent anti-microbial properties can be a crucial asset in decreasing the chance of infection and/or contamination. Additionally, chitosan, when biological burden is removed, is biodegradable and biocompatible with low toxicity to mammalian cells.

Chitosan has positive charges along its backbone that cause it to interact electrostatically with negatively charged pharmaceuticals (e.g., blood cells), thus creating a sticky interface between chitosan and any potential ocular wound providing hemostasis. Carboxymethyl chitosan, succinyl chitosan, glycol chitosan, thiolated chitosan can be used to reduce the requirements for acid solubilization. Chitosan is a linear polymer of glucosamine units. Structurally, it is distinguished from cellulose by the presence of the primary amine group. Chitosan is available commercially in various grades and average molecular weights (e.g., Sigma Aldrich®).

Chitosan may be derivatized by utilizing the reactivity on the amino group and or hydroxyl groups. Some exemplary chitosan derivatives may include N-pathaloylation of chitosan, dendronized chitosan-sialic acid hybrids, methylthiocarbamoyl and phenylthiocarbamoyl chitosans, lactic/glycolic acid chitosan hydrogels, or nanocomposite from natural polysaccharide chitosan. In some aspects, chitosan may be hydrophobically-modified. A chitosan can be hydrophobically-modified using standard techniques in the art. In certain aspects, chitosans can be hydrophobically-modified by reaction of alkyl (or aryl) aldehydes with primary amine groups along the chitosan backbone (i.e., in a 50/50 (v/v) % of aqueous acetic acid and ethanol). After reaction, the resulting Schiff bases or imine groups can be reduced to stable secondary amines by dropwise addition of a reducing agent. In other aspects, the chitosan can be hydrophobically-modified through the addition of palmitic anhydride to the chitosan.

By "co-administer" it is meant that a composition described herein is administered at the same time, just prior to, or just after the administration of additional therapies. The composition of the disclosure can be administered alone or can be co-administered with a second composition/therapeutic agent to a subject. Co-administration is meant to include simultaneous or sequential administration of the composition individually or in combination with a second composition/therapeutic agent.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "concurrent administration" includes overlapping in duration at least in part. For example, when two agents (e.g., any of the compositions described herein) are administered concurrently, their administration occurs within a certain desired time. The compositions' administration may begin and end on the same day. The administration of one composition can also precede the administration of a second composition by day(s) as long as both compositions are taken on the same day at least once. Similarly, the administration of one composition can extend beyond the administration of a second composition as long as both compositions are taken on the same day at least once. The compositions do not have to be taken at the same time each day to include concurrent administration.

As used herein, the term, "cream" may refer to a thick (high viscosity) liquid or semi-liquid that may be used for therapeutic treatment of a disease, syndrome, or condition (i.e., dry eye syndrome). Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

As used herein, "digital mechanism" may refer to a means by which a non-permeable membrane can be broken on demand by a user, wherein the user may press a button on the delivery device (100) and thereby allowing mixing of the Chamber A (101) and Chamber B (102) within the delivery device (100).

The term, "dry eye" or "dry eye syndrome" may refer to an ophthalmic syndrome or ocular surface condition. Dry eye or dry eye syndrome include keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LNE). Dry eye and tear film instability can damage the ocular surface. It is accompanied by increased osmolarity of the tear film and inflammation of the ocular surface. An increase in tear osmolarity, which causes ocular surface inflammation, is thought to be the central pathogenic mechanism of dry eye.

Dry eye syndrome is a large and growing problem and is very common with an estimated 25% of patients in general ophthalmology or optometry clinics reporting symptoms of dry eye. It has multiple causes that result in an unstable tear film and rapid tear film breakup time. It is known that the incidence of dry eye syndrome increases with age and has a higher prevalence in women relative to men. Currently, there is no cure for dry eye syndrome. Common treatments are targeted to manage the symptoms. The mainstay of conventional therapy is the application of artificial tears that increase moisture on the ocular surface, and provide additional lubrication. A variety of artificial tear formulations differ from each other in their electrolyte composition, osmolarity, viscosity, presence or absence of preservatives, and compatible solutes. However, frequent application of artificial tears containing preservatives to prevent contamination has been found to include both toxic and allergic reactions, especially in patients with sensitive eyes. Additional therapies for dry eye syndrome are also inadequate. These therapies include immunomodulators (e.g. Restasis®, Xiidra®) and corticosteroids. They tend to only address the symptoms, rather than the cause of the disease with corticosteroids in particular having the risk of causing cataracts and glaucoma.

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

As used herein, "electrochemical mechanism" may refer to a means by which a non-permeable membrane can be broken on demand by a user, wherein the user introduces an electromechanical signal (i.e. voltage or current signals) on the delivery device (100) and thereby allowing mixing of the Chamber A (101) and Chamber B (102) within the delivery device (100).

"Emulsion" as used herein may include a fine dispersion of minute droplets of one liquid in another in which it is not soluble or miscible. Alternatively, "emulsion" may refer to a mixture of two or more liquids that are normally immiscible (unmixable or unbendable). Emulsions are part of a more general class of two-phase systems of matter called colloids.

The term, "freeze-dried" or "lyophilized" refers to a dehydration process typically used to preserve a perishable material or make the material more convenient for transport. Freeze-drying works by freezing the material and then reducing the surrounding pressure to allow the frozen water in the material to sublimate directly from the solid phase to the gas phase. If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance. Freeze-drying also causes less damage to the substance than other dehydration methods using higher temperatures. Freeze-drying does not usually cause shrinkage or toughening of the material being dried. Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. By removing the water from the material and sealing the material in a vial, the material can be easily stored, shipped, and later reconstituted to its original form for injection. Freeze-drying can also be used to increase the shelf life of some pharmaceuticals for many years.

As used herein, "gamma irradiation" refers to a means of pathogen reduction. Gamma rays are a form of electromagnetic radiation with higher energy than x-rays. The primary industrial sources of gamma rays are radionuclide elements such as Cobalt 60, which emit gamma rays during radioactive decay. Gamma rays pass readily through plastics and kill bacteria by breaking the covalent bonds of bacterial DNA. They are measured in units called kiloGrays (kGy). Gamma irradiation between, for example, 10 and 50 kGy, may be performed to the serum or plasma at 4° C. before and/or after it is freeze-dried. This inactivates potential pathogens including viruses that may not have been previously eradicated. An additive (i.e., ascorbic acid or glycine) may be added as a protectant for plasma proteins against gamma irradiation and for pH balance. In some examples, gamma irradiation may be performed to the serum or plasma before it is freeze-dried. The gamma irradiated liquid serum or plasma may be stored and frozen at minus 70° C. for future pathogen reduction and/or freezing drying. In other examples, gamma irradiation may be performed to the serum or plasma after it is freeze-dried. The gamma irradiated freeze-dried serum or plasma may be stored and frozen at minus 70° C. for future pathogen reduction.

The term, "gel" as used herein may refer to a material which is not a readily flowable liquid and not a solid, i.e., semi-solid. Gels may be formed from naturally occurring or synthetic materials. The gels can be non-ordered to slightly ordered showing some birefringence, liquid crystal character. Gels maybe produced using a suitable gelling agent including, but not limited to, gelatin, tragacanth, or a cellulose derivative and may include glycerol as a humectant, emollient, and preservative. Gels are administered topically or, for example, after shaking, in the form of a hydrogel as an eye drop.

As used herein, "intermittent administration" includes the administration of a composition for a period of time (which can be considered a "first period of administration"), followed by a time during which the composition is not taken or is taken at a lower maintenance dose (which can be considered "off-period") followed by a period during which the composition is administered again (which can be considered a "second period of administration"). Generally, during the second phase of administration, the dosage level of the composition will match that administered during the first period of administration but can be increased or decreased as medically necessary.

"Jelly" according to the current disclosure is a class of gels, which are semisolid systems that consist of suspensions made up either small inorganic particles or large organic molecules interpenetrated by a liquid, in which the structural coherent matrix contains a high portion of liquid, usually water.

"Liquid" as used herein is a dosage form consisting of a composition in its liquid state. A liquid is pourable; it flows and conforms to its container at room temperature. Liquids display Newtonian or pseudoplastic flow behavior. In embodiments, a "semi-liquid" as used herein may have properties of both a liquid and another formulation (i.e., a suspension, an emulsion, a solution, a cream, a gel, a jelly, and the like).

The term "linear biopolymer" as used herein may refer to polymers produced by living organisms (e.g., biopolymers) that are connected in a straight chain of repeat monomeric subunits.

"Lubricating" or "lubricant" as used herein may refer to reducing the friction between two surfaces (i.e., non-keratinized surfaces). Lubricants prevent ingredients from sticking together. Common minerals like talc or silica, and fats, e.g. vegetable stearin, magnesium stearate or stearic acid are the most frequently used lubricants in tablets or hard gelatin capsules. Lubricants are agents added in small quantities to tablet and capsule formulations to improve certain processing characteristics. Other roles of lubricants include an anti-adherent role and a glidant role (i.e., to enhance product flow). Lubricants can be both hydrophilic and hydrophobic. In general, most widely used lubricants are hydrophobic. Hydrophobic lubricants are generally good lubricants and are usually effective at relatively low concentrations. Many also have both anti-adherent and glidant properties. For these reasons, hydrophobic lubricants are used much more frequently than hydrophilic compounds. Examples include magnesium stearate.

The term "moisturizing", as used herein, refers to improving hydration of a non-keratinized surface, such that water-binding capacity of the surface increases. The term "moisturize" or derivatives thereof, relates to the conversion or enhancement of the water contents of non-keratinized surfaces of a subject. The term "humectant" is used herein in its usual sense, refers to water-soluble, physiologically acceptable, substances which are hygroscopic and capable of spontaneously absorbing water vapor. "Occlusion" is a term used herein to indicate the trapping of water in the non-keratinized surfaces by a layer of water-impervious fatty substance. Exemplary vaginal moisturizers include, but are not limited to, Replens®, K-Y Liquibeads®, Lubrin®, Astroglide Silken Secret® and Vitamin E gel. Examples of oral moisturizes (i.e. for dry mouth) may include, but are not limited to, artificial saliva products, saliva stimulants, Salese Soothing®, Orajel®, and Eucerin® cream. Exemplary moisturizers for diabetic ulcers and/or chronic wounds may include any saline or similar dressings that provide a moist environment, TriDerma® MD Ulcer Healing Cream, or Neoteric Diabetic Healing Cream®.

The term "non-autologous" as used herein may refer to denoting, relating to, or involving tissues or cells (including plasma or serum) that are not originated from the recipient (i.e., a subject in need of a treatment with the tissues or cells). In contrast, "autologous," as used herein, is in its ordinary meaning cells, tissues (including plasma or serum) obtained from the same individual, i.e., the recipient's own plasma or serum, and does not include plasma or serum originating from another individual (i.e., umbilical cord plasma or serum may be included as non-autologous). Autologous plasma or serum is usually not readily available from a blood bank or a central repository unless it has been previously donated by the recipient. The term "allogenic" or "homologous" is used here by its ordinary meaning, i.e., denoting, relating to, or involving tissues or cells (including plasma or serum) that are genetically dissimilar and hence immunologically incompatible, although from individuals of the same species. Allogenic plasma or serum is, therefore, encompassed by the term "non-autologous" plasma or serum. In some examples, non-autologous plasma or serum may be purchased from a Blood Bank.

As used herein, "ocular surface disorder" "ophthalmic disease," "ophthalmic disorder," and the like, includes, but is not limited to, dry eyes, epithelial defects, Superior limbic keratoconjunctivitis, keratoconjunctivitis sicca, Neurotrophic keratopathy, Sjögren's syndrome, Stevens-Johnson syndrome, Ocular cicatricial pemphigoid, Medicamentosa, Graft-versus-host disease, and corneal ulcerations and erosions.

The term, "non-permeable membrane" describes a barrier separating two environments (i.e. Chamber A (101) and Chamber B (102) of the ophthalmic therapeutic agent delivery device (100) including the freeze-dried non-autologous plasma or serum and a reconstitution fluid, respectively), whereby nothing passes in-between the two environments. The non-permeable membrane as described herein may be broken by a user, for example, by a digital mechanism, an electromechanical mechanism, or agitation or twisting.

"Ocular surface" as used herein includes the cornea and the conjunctiva. The ocular surface is covered by a thin layer of fluid or tear film. The tear film is not only responsible for the majority of the refractive power of the eye (approximately two-thirds) and clear vision, it is also responsible for nourishing the cells on the surface of the eye and preventing infection. It is the first line of defense against foreign pathogens and supports healing. Since the surface epithelium of the eye is similar to other external surfaces of the body and regularly refreshes itself by shedding its epithelial cells, the tears play a vital role in the health of this process. The surface of the eye can suffer many kinds of diseases. One of most common diseases of the surface of the eye is dry eye syndrome.

"Ocular surface conditions" as used herein may include any condition of the surface of the eye (e.g., conjunctiva and cornea). The conditions may include, but are not limited to, dry eye, epithelial defects, Superior limbic keratoconjunctivitis, Keratoconjunctivitis sicca, Neurotrophic keratopathy, Sjögren's syndrome, Stevens-Johnson syndrome, Ocular cicatricial pemphigoid, Medicamentosa and Graft-versus-host disease.

Ocular surface surgery" may include penetrating keratoplasty and refractive surgery laser-assisted in situ keratomileusis (LASIK), laser epithelial keratomileusis (LASEK), or photorefractive keratectomy (PRK).

As used herein the term "ophthalmic composition" refers to a composition intended for application to the eye or its related or surrounding tissues such as, for example, the eyelid or onto the cornea. The term also includes compositions intended to therapeutically treat conditions of the eye itself or the tissues surrounding the eye. The ophthalmic composition can be applied topically or by other techniques, known to persons skilled in the art, such as injection to the eye. Examples of suitable topical administration to the eye include administration in eye drops and by spray formulations. A further suitable topical administration route is by subconjunctival injection. The compositions can also be provided to the eye periocularly or retro-orbitally.

As used herein, an "ophthalmic therapeutic agent delivery device" may incorporate the compositional elements described herein (e.g., the freeze-dried non-autologous plasma or serum polymer, and reconstitution fluid).

As used herein, the term "ointment" may refer to a highly viscous liquid or semi-liquid formulation that may be used for therapeutic treatment of a disease, syndrome, or condition (i.e., dry eye syndrome).

"Patient," "subject," "patient in need thereof," and "subject in need thereof" are herein used interchangeably and refer to a living organism suffering from or prone to a disease or condition that can be treated by administration using the methods and compositions provided herein. Non limiting examples include humans, other mammals, bovines, rats, mice, dogs, monkeys, goat, sheep, cows, deer, and other non-mammalian animals. In some embodiments, a patient is human.

"Pessaries" or "pessary" as used herein may refer to a solid unit-dose form suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol®), polyethylene glycols (macrogols), and glycerol suppository basis.

"Plasma" as used herein may refer to a fluid substance in blood that is the pale straw colored liquid component of blood that normally holds the blood cells in whole blood in suspension; this in turn makes plasma the extracellular matrix of blood cells. It mostly consists of water (up to 95% by volume), and contains dissolved proteins, (including, for example, serum albumins, globulins, and fibrinogen), glucose, clotting factors, electrolytes (e.g., $Na^+$, $Ca_2^+$, $Mg_2^+$, $HCO_3^-$, $Cl^-$), hormones, and carbon dioxide (plasma being the main medium for excretory product transportation). Plasma also serves as the protein reserve of the human body. It plays a vital role in an intravascular osmotic effect that keeps electrolytes in balanced form and protects the body from infection and other blood disorders. In embodiment, "plasma" is an engineered composition including components of natural human plasma.

The term "polymer" as referred to herein is meant as a macromolecule, composed of many repeated subunits called monomers. The word polymer designates an unspecified number of monomer units. When the number of monomers is very large, the compound is sometimes called a high polymer. Polymers are not restricted to monomers of the same chemical composition or molecular weight and structure. Some natural polymers are composed of one kind of monomer. Most natural and synthetic polymers, however, are made up of two or more different types of monomers. Such polymers are known as copolymers. Polymers can be linear or branched. For example, a linear polymer characterized by a repetition of ester groups along the backbone chain is called a polyester.

Exemplary natural polymeric materials include shellac, amber, wool, silk, rubber, and cellulose. Non-natural (e.g., synthetic) polymers include synthetic rubber, phenol formaldehyde resin, neoprene, nylon, polyvinyl chloride, polystyrene, polyethylene, polypropylene, and silicone.

Additional synthetic polymers that can be used include biodegradable polymers such as poly(lactide) (PLA), poly (glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, Teflon®, and nylon. A non-absorbable polyvinyl alcohol sponge is available commercially as Ivalon™, from Unipoint Industries.

The term, "polycation" or "cationic" refers to a compound or molecule described herein (e.g., polymers such as chitosan and chitosan derivatives) that may be protonated and thereby having an overall positive charge. The protonation may be, for example, on the amino groups of the compound or molecule (e.g., polymers such as chitosan and chitosan derivatives) and can then subsequently form ionic complexes with a wide variety of natural or synthetic anionic species, including for example, lipids, proteins, DNA and other negatively charged synthetic polymers (e.g., poly (acrylic acid)). Chitosan, for example, is the only positively charged, naturally occurring polysaccharide.

Polysaccharides are polymeric carbohydrate structures, formed from repeating units joined together with glycosidic bonds. Their structures are often linear, but may contain various degrees of branching. In nature, polysaccharides have various resources from algal origin, plant origin, microbial origin and animal origin. Polysaccharides have a general formula of $C_x(H_2O)_y$ where x is usually a large number between 200 and 2500. Considering that the repeating units in the polymer backbone are often six-carbon monosaccharides, the general formula can also be represented as $(C_6H_{10}O_5)n$ where $40 \leq n \leq 3000$.

Examples of monosaccharides are glucose, fructose, and glyceraldehyde. Examples of naturally occurring polysaccharides are: cellulose, dextrin, pectin, alginic acid, agar, agarose, and carragenas. Naturally occurring polysaccharides are usually acidic in nature.

In embodiments, polysaccharides may contain more than ten monosaccharide units. Polysaccharides are an important class of biological polymers. Their function in living organisms is usually either structure- or storage-related. Cellulose and chitin are examples of structural polysaccharides. Cellulose is used in the cell walls of plants and other organisms, and is said to be the most abundant organic molecule on Earth. Chitin has a similar structure to cellulose, but has nitrogen-containing side branches, increasing its strength. It is found in arthropod exoskeletons and in the cell walls of some fungi. It also has multiple uses, including surgical threads. Polysaccharides also include callose or laminarin, chrysolaminarin, xylan, arabinoxylan, mannan, fucoidan and galactomannan.

The terms "prevent," "preventing," or "prevention," "prophylactic treatment" and the like, refer to reducing the probability of developing a disorder or condition in a subject, who does not have, but is at risk of or susceptible to developing a disorder or condition. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

"Psoralen" or "psoralene" is the parent compound in a family of natural products known as furocoumarins. It is structurally related to coumarin by the addition of a fused furan ring, and may be considered as a derivative of umbelliferone. It is widely used in PUVA (psoralen+UVA) treatment for psoriasis, eczema, vitiligo, and cutaneous T-cell lymphoma. Psoralens are often used for the inactivation of pathogens in blood products. The synthetic amino-psoralen, amotosalen HCl, has been developed for the inactivation of infectious pathogens (bacteria, viruses, protozoa) in platelet and plasma blood components prepared for transfusion support of patients. A photoactive solvent or detergent is mixed into the serum or plasma and exposed to ultraviolet light. With amotosalen HCl, for example, photoactivation occurs when the mixture is illuminated with UVA treatment at 3 J/cm$^2$. This reduces the risk of transfusion-associated transmission of viruses, bacteria, and parasites that theoretically may be present.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may include 1 to 10, 1 to 20, 1 to 30, and 1 to 40 in one direction, or 50 to 40, 50 to 30, 50 to 20, and 50 to 10 in the other direction.

"Reconstitution" as referred to herein means in its ordinary sense, to return a dehydrated or concentrated composition to the liquid state by adding a liquid.

As used herein, "reconstitution fluid" may refer to any solvent described herein used to reconstitute the freeze-dried composition of the current disclosure. In exemplary embodiments, water or a saline solution (e.g. 0.9% w/v sodium chloride for injection) may be used, any additives may be included, into the reconstitution fluid (i.e., glycine or ascorbic acid, or chitosan, alginate, and gelatin), and serum may also be used as a reconstitution fluid. In embodiments, the solvents used for the reconstitution fluid may be sterile.

The reconstituted freeze-dried composition may be reconstituted as a solution, suspension, semi-liquid, emulsion, ointment, cream, or semi-solid gel.

As used herein, "salts" or "salt form" or "pharmaceutically accepted salts" may include base addition salts (formed with free carboxyl or other anionic groups) which are derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts are formed as acid addition salts with any free cationic groups and generally are formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure may include amine salts formed by the protonation of an amino group with inorganic acids such as hydrochloric acid, hydrobromic acid, hydroiodic acid, sulfuric acid, phosphoric acid, and the like. Salts of the disclosure also include amine salts formed by the protonation of an amino group with suitable organic acids, such as p-toluenesulfonic acid, acetic acid, and the like. Additional excipients which are contemplated for use in the practice of the present disclosure are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference.

The "semisolid gel" according to the current disclosure is a semisolid. The semisolid formulation apparent viscosity may increase with concentration.

As used herein, "sequential administration" includes that the administration of two agents (e.g., compositions described herein) occurs separately on the same day or do not occur on a same day (e.g., occurs on consecutive days).

The term, "serum" as used herein is the component that is neither a blood cell (serum does not contain white or red blood cells) nor a clotting factor. Serum is a protein-rich liquid that separates out when blood coagulates; i.e., serum refers to components wherein fibrinogens, clotting factors, etc. . . . are removed from the blood plasma. Serum includes all proteins not used in blood clotting and all the electrolytes, antibodies, antigens, hormones, and any exogenous substances (e.g., drugs and microorganisms). Blood is centrifuged to remove cellular components. Anti-coagulated blood yields plasma containing fibrinogen and clotting factors. Coagulated blood yields serum without fibrinogen, although some clotting factors remain. In embodiments, "serum" is an engineered composition including components of natural human serum.

"Solution" according to the current disclosure is a clear, homogeneous liquid dosage form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage upon administration and good accuracy when the solution is diluted or otherwise mixed.

The term "solvent," as used herein, refers to a liquid solvent either aqueous or non-aqueous. The selection of the solvent depends notably on the solubility of the composition on said solvent and on the mode of administration. Aqueous solvent may consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol. As used herein, serum may be used as a solvent for reconstitution of the freeze-dried composition described herein.

"Suspension" as used herein is a liquid dosage form that contains solid particles dispersed in a liquid vehicle.

"As used herein, the term "syndrome" may refer to a group of symptoms that consistently occur together or a condition characterized by a set of associated symptoms. A syndrome (e.g., dry eye syndrome) may be a set of medical signs and symptoms that are correlated with each other and often, are correlated with a specific disease. A disease on the other hand, may be a health condition that has a clearly defined reason behind it. A syndrome (from the Greek word meaning 'run together') however, may produce a number of symptoms without an identifiable cause. They may suggest the possibility of an underlying disease or even the chances of developing a disease.

"Tear breakup time" or "TBUT" or "tear film breakup time" or "TFBUT" as used herein may refer to a clinical test that measures the interval between the individual's last complete blink and the breakup of the tear film. The test may be used to assess for dry eye syndrome. To measure TBUT, fluorescein is instilled into the patient's tear film and the patient is asked not to blink while the tear film is observed under a broad beam of cobalt blue illumination. The TBUT is recorded as the number of seconds that elapse between the last blink and the appearance of the first dry spot in the tear film.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The term "umbilical cord blood" or "cord blood" as used herein generally refers to blood obtained from the placenta and the umbilical cord after child birth. This blood originates from the neonate and is no longer needed by the newborn and is commonly discarded, for example, cord blood may refer to blood which is obtained from the umbilical cord or placenta of newborns. The use of cord or placental blood can be obtained relatively easily and without trauma to the donor. Cord blood is preferably obtained by direct drainage from the umbilical vein of a discarded placenta. For example, the umbilical cord blood may be obtained from mothers with vaginal or cesarean section delivery.

The term "umbilical cord blood serum" or "cord serum" generally refers to umbilical cord blood in which the cells have been removed so that the cord serum is substantially free of whole cells. Umbilical cord blood serum contains a high concentration of tear components, growth factors, neurotrophic factors, vitamin A, fibronectin, prealbumin, and oil. Umbilical cord serum can provide basic nutrients for epithelial renewal and can facilitate the proliferation, migration, and differentiation of the ocular surface epithelium.

The term "vaginal ring" as used herein may refer to a thin and/or flexible ring that is inserted into the vagina. In some examples, the active agent (e.g., reconstituted freeze-dried composition described herein) may be controlled-release/sustain-release.

The term "vial" or "container", as used herein, refers broadly to a reservoir suitable for retaining the plasma or serum composition in lyophilized form. Similarly, it will retain the solvent for reconstitution. Examples of a vial that can be used in the present disclosure include syringes, ampoules, cartridges, or other such reservoir suitable for delivery of the plasma or serum composition to the patient. Alternatively, the vial retaining the plasma or serum composition the one retaining the solvent for reconstitution can be presented as the 2 compartments of a dual-chamber system (syringe or cartridge for example). Vials suitable for packaging products for ophthalmic administration are well known and recognized in the art.

As used herein, "viscosity" refers to a fluid's resistance to flow.

The term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 ml of the component dissolved in a 100 ml of solvent. The term "weight/volume percent" or "% (w/v)" refers to a percentage of a component in a solution that is calculated on the basis of weight for the component and on the basis of volume for the solvent. For example, a 1.0% (w/v) solution of a component would have 1 g of the component dissolved in a 100 ml of solvent.

COMPOSITION

In one aspect, the present disclosure includes a freeze-dried composition including non-autologous plasma or serum and a polymer. In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof.

In embodiments, the present disclosure includes a freeze-dried composition including non-autologous serum and a polymer for treating dry eye syndrome or for moisturizing and/or repairing non-keratinized surfaces (e.g., dry mouth syndrome, vaginal dryness, diabetic ulcers and other chronic wounds), wherein the polymer has a molecular weight of 100 to 1200 kDA, or derivatives thereof.

In embodiments, the serum or plasma is freeze-dried together with the polymer to form a freeze-dried composition. In alternative embodiments, the serum or plasma can be freeze-dried separately from the polymer, which may or may not also be freeze-dried.

In embodiments, the disclosure provides a freeze-dried composition comprising non-autologous plasma or serum and a polysaccharide having a molecular weight of 100 to 1200 kDa, preferably from 100 to 400 kDa, or a polysaccharide having a molecular weight of 100, 250, or 400 kDa, wherein the polysaccharide is chitosan, or a hydrophobically modified chitosan. In embodiments, the composition preferably comprises non-autologous serum. In embodiments, the freeze-dried composition is biodegradable and biocompatible. In embodiments, the freeze-dried composition is in the form of a cohesive solid material, such as a wafer or sheet. In embodiments, the freeze-dried composition in the form of a cohesive solid material is further combined with a sufficient amount of an aqueous liquid (e.g., a reconstitution fluid). In embodiments, the reconstitution fluid is any solvent described herein. In exemplary embodiments, water or a saline solution may be used as the reconstitution fluid, any additives may be included (e.g., glycine or ascorbic acid), and in additional embodiments, liquid serum may also be used as a reconstitution fluid to form a cohesive sponge-like solid material. In embodiments where liquid serum or plasma is used, the serum or plasma may optionally be diluted with an acceptable carrier, such as water or an aqueous buffer, e.g., saline. In another embodiment, the freeze-dried composition in the form of a powder which can be formulated into a suitable dosage form for application to a non-keratinized epithelial surface, such as the surface of the eye, mouth, or vagina, or the surface of an external wound. Such powder compositions may be formulated, for example, as a liquid, gel, or ointment.

In one aspect, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA and a formula including of Formula 1: $[[R_1]m\text{-}L\text{-}[R_2]n]p$, or derivatives thereof, where $R_1$ and $R_2$ are units of the polymer, m is an integer from 1-10,000, n is an integer from 1-10,000, and p is an integer from 10-10,000, L is a bond. In some embodiments, "m" and "n" of Formula I is 1.

In embodiments, freeze-dried composition includes umbilical cord plasma or serum. In embodiments, the polymer in the composition is a high molecular weight (e.g. 100 to 1200 kDA) polymer such that the composition upon administration to the eye is retained on the ocular surface due to the impermeability of the polymer through one or more layers of the cornea, conjunctiva, and sclera. In embodiments, the polymer included in the composition is chitosan. The polymer increases the ocular surface retention of the composition such that upon administration to an eye of a subject having dry eye syndrome, the composition is retained on the ocular surface for about 4 hours to about 24 hours.

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and chitosan or derivatives thereof. In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including mammalian (e.g., human) umbilical cord plasma and chitosan or derivatives thereof. In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including mammalian (e.g., human) umbilical cord serum and chitosan or derivatives thereof. In some embodiments, the non-autologous plasma or serum includes allogenic or homologous plasma or serum, respectively.

Blood plasma or serum used in the composition of the present disclosure may include plasma or serum isolated from blood of all species of mammals including humans, sheep, goats, pigs, horses, dogs and cattle, primates, and rodents. In an embodiment of the present disclosure, blood plasma or serum used in the composition can be purchased from a Blood Bank. In some embodiments, the non-autologous plasma or serum of the present disclosure may be from umbilical cord plasma or serum.

In embodiments, the composition includes plasma or serum (e.g., human umbilical cord plasma or serum) from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight of the composition, and any range in between.

In embodiments, the freeze-dried composition contains from about 10-90 wt % plasma or serum (e.g., human umbilical cord plasma or serum) components, or from 10-90 wt %, 20-90 wt %, 30-90 wt %, 40-90 wt %, 50-90 wt %, 60-90 wt % plasma or serum components. In embodiments, the composition contains about 40 wt %, about 50 wt %, about 60 wt %, about 70 wt %, or about 80 wt % plasma or serum components. In an embodiment, the freeze-dried composition contains about 75 wt % plasma or serum components. In the context of these embodiments, preferably the remainder of the weight percentage of the composition is made up of a polysaccharide, preferably chitosan or a hydrophobically modified chitosan. In certain embodiments, the composition may further contain small amounts of additional additives or excipients, typically in a range of less 10 wt % collectively, preferably less than 5 wt % or less than 2 wt %, based on the total dry weight of the composition.

In embodiments, the composition of the present disclosure includes one or more polymers. For example, the polymer included in the composition includes a low molecular weight polymer, a medium molecular weight polymer, or a high molecular weight polymer. Low molecular weight polymers may include for example, polymers of approximately 100 kDa or less (e.g., approximately 10 kDa to approximately 100 kDa). Medium weight polymers may include, for example, polymers of approximately 250 kDa or between 100 and 350 kDa, whereas high molecular weight polymers may include polymers of about 400 kDa or from about 400 to 1200 kDa. In embodiments, the composition of the present disclosure includes ultra-high weight polymers, and may include polymers of greater than 1000 kDa. In embodiments, the molecular weight of the polymer is in a range from about 100 kDa to about 1200 kDa, from about 100 kDa to about 200 kDa, from about 100 kDa to about 300 kDa, from about 100 kDa to about 400 kDa, from about 100 kDa to about 500 kDa, from about 100 kDa to about 600 kDa, from about 100 kDa to about 700 kDa, from about 100 kDa to about 800 kDa, from about 100 kDa to about 900 kDa, from about 100 kDa to about 1000 kDa, from about 100 kDa to about 1100 kDa, from about 100 kDa to about 1200 kDa, and any weight there between.

In embodiments, the polymer is a chitosan and has a molecular weight of from 100 to 400 kDa, or a molecular weight of 100, 250, or 400 kDa.

In embodiments, the polymer is a biopolymer, e.g., cellulose, starch, lignin, chitin, and various polysaccharides. In embodiments, the polymer is a polycationic polymer with positive charges at several sites, for example, along the backbone of chitosan and its derivatives. In embodiments, the polymer is chitosans, alginates, gelatins, or any combination(s) thereof. In embodiments, the polymer is, for example, one or more hydrophobically modified polysaccharides.

In embodiments, the polymer (e.g., chitosans, alginates, or gelatins) is added to the composition in any suitable amounts. For example, in some embodiments, polymer is in a concentration of from about 0.025% to about 2.0% by weight of the composition. The polymer can be present at about 0.025, about 0.05, about 0.1, about 0.2, about 0.3, about 0.4, about 0.5, about 1.0, and about 2.0 percent by weight or any amount in between these amounts of the composition. In an embodiment, the polymer is added at a concentration of about 0.05% (w/v) to about 1.0% (w/v) of the composition. In embodiments, the ratio of the non-autologous plasma or serum to the polymer in the composition is 1:1, 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 3:1, 4:1, 5:1, 6:1, 7:1, 8:1, 9:1, 10:1, or any ratio integers in between, and/or vice versa.

In embodiments, the polymer of the present composition may include chitosan or derivatives thereof. For example, the composition includes salts or derivatives of chitosan. Salts of chitosan include organic and inorganic acid salts, for example, glutamate, lactate, citrate, hydrochloride, succinate, maleate, ascorbate, propionate, formate, carbonate and acetate salts. Derivatives of chitosan include hydrophobically-modified chitosan, succinyl chitosan, carboxymethyl chitosan, glycol chitosan, sulfonated chitosan, thiolated chitosan or chitosan modified with quaternary ammonium groups.

In embodiments, the polymer is a chitosan, and in certain embodiments, the chitosan is a hydrophobically-modified (hm) chitosan. A chitosan can be hydrophobically-modified using standard techniques in the art. In certain aspects, chitosans can be hydrophobically-modified by reaction of alkyl (or aryl) aldehydes with primary amine groups along the chitosan backbone (i.e., in a 50/50 (v/v) % of aqueous acetic acid and ethanol). After reaction, the resulting Schiff bases, or imine groups, can be reduced to stable secondary amines by dropwise addition of a reducing agent. In other aspects, the chitosan can be hydrophobically-modified through the addition of palmitic anhydride (i.e., using 0.1 g dissolved into 20 mL of ethanol) to the chitosan (i.e., wherein the chitosan is dissolved in a 50/50 (v/v) mixture of acetic acid).

In embodiments, the hydrophobic substituents of the hydrophobically modified chitosan are provided by palmitic anhydride. In embodiments, the disclosure provides a freeze-dried composition comprising plasma or serum and a polysaccharide selected from chitosan, a hydrophobically modified chitosan, sucrose, or trehalose, wherein the composition comprises from about 60-90 wt % of the plasma or serum components and from about 10-40 wt % of the polysaccharide.

In embodiments of the freeze-dried compositions described here in which the chitosan is a hydrophobically modified chitosan, the chitosan may be hydrophobically-modified by reaction of alkyl (or aryl) aldehydes with primary amine groups along the chitosan backbone in a 50/50 (v/v) % of aqueous 0.2 M acetic acid and ethanol, as described in US 20160206777. As described in US 20160206777, after reaction, the resulting Schiff bases, or imine groups, are reduced to stable secondary amines by dropwise addition of the reducing agent sodium cyanoborohydride. Hydrophobically modified chitosans, and methods for making them, are also described in U.S. Pat. Nos. 9,616,088 and 8,932,560, the disclosures of which are hereby incorporated by reference.

In embodiments of the freeze-dried compositions described here in which the chitosan is a hydrophobically modified chitosan, up to 10% of the available amines of the chitosan backbone are substituted with the hydrophobic substituent. In embodiments, between 1.5% and 4.5% of available amines are substituted.

In embodiments, the hydrophobically-modified chitosan of the composition described here is selected from the group consisting of chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, and chitosan glycolate.

In embodiments, the polymer of the present composition is a polysaccharide selected from the group consisting of chitosan, cellulose, dextrin, pectin, alginic acid, agar, agarose, and carragenas, and derivatives thereof. In embodiments, the polysaccharide is chitosan, or a derivative thereof, preferably a hydrophobically modified chitosan. Chitosan is enzymatically degraded in vivo by several enzymes with the main enzyme being lysozyme which is a non-specific protease present in all mammalian tissues. Human lysozyme is part of the human body's defense against some bacteria. Chitosan is enzymatically degraded by lysozyme into non-toxic oligosaccharides that can be either excreted or incorporated into glycosoaminoglycans and glycoproteins. Lysozyme is present in almost all body and maternal fluids including blood serum, umbilical cord blood serum, amniotic fluid, saliva, gastric juice, tears and mucous membranes. Activity is normally from 7 to 13 mg/L in serum and 120 times higher in tears. Gastric juice has about 8 times more than in normal serum. Chitosan is both biodegradable and biocompatible. Chitosan is also chemically versatile and mimics the extracellular matrices of tissues that are made up of various glycosaminoglycans. This makes chitosan and its derivatives especially advantageous for tissue engineering and drug delivery due to their ability to act as molecular scaffolds. Drugs within the chitosan matrix can be slowly released to the diseased target as the chitosan is biodegraded by endogenous lysozyme and other enzymes.

Exemplary beneficial properties of chitosan and its derivatives include anti-microbial properties, biodegradability, biocompatibility, and nontoxic properties. Furthermore, the mucoadhesive properties and viscosity of chitosan or derivatives thereof may readily be modified, for example by choice of a low, medium, or high molecular weight chitosan as described herein. Generally, as described in the examples, both mucoadhesiveness and viscosity of the polymer-containing compositions of the disclosure increase with increasing molecular weight of the chitosan polymer. The molecular weight of chitosan can vary between 10-100,000 kDa. Preferably, the compositions described here contain chitosan, or a hydrophobically modified chitosan of a molecular weight ranging from 100 to 400 kDa, or 100, 250, or 400 kDa. The anti-microbial properties of chitosan and its derivatives may be against bacteria, yeast, fungi, and viruses. The anti-microbial effect is believed to be chitosan's ability to breakdown the microorganism wall, thereby causing it to leak and eventually killing the microorganism.

As described above, the mucoadhesive properties and viscosity of chitosan may be readily modified. Chitosan is a linear polysaccharide composed of linked glucosamine units. The ability to change the molecular structure of chitosan by varying degrees allows its properties to be modified. One property of chitosan is the immense structural possibilities for chemical and mechanical modifications to generate novel properties, functions and applications. Even though molecular weight has a profound effect on the properties of chitosan, deacetylation, or the addition of different functional groups can also change its properties, e.g., depolymerized chitosans are more water-soluble.

The chitosan has the following backbone chemical structure, where n represents any integer and represents the number of monomeric units in the chitosan chain (i.e., the degree of polymerization).

Formula I

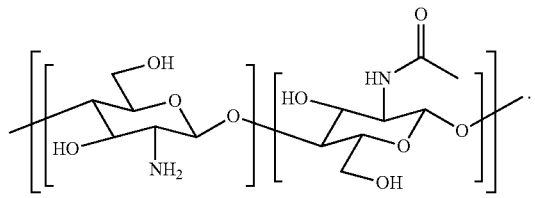

In embodiments, the composition of the present disclosure includes chitosan derivatives, for example, but is not limited to, esters, ethers or other derivatives formed by bonding acyl and/or alkyl groups with the hydroxyl groups. Additional examples of chitosan derivatives include O-alkyl ethers of chitosan and O-acyl esters of chitosan. In embodiments, the composition of the present disclosure includes modified chitosans, such as those conjugated to polyethylene glycol may be used in the present disclosure. Conjugates of chitosan and polyethylene glycol are described in WO99/01498 and incorporated herein by reference. In embodiments, the composition of the present disclosure includes chitosan derivatives, for example, N-pathaloylation of chitosan, dendronized chitosan-sialic acid hybrids, methylthiocarbamoyl and phenylthiocarbamoyl chitosans, lactic/glycolic acid chitosan hydrogels, or nanocomposite from natural polysaccharide chitosan.

The chitosan, chitosan derivative, or salt in the composition of the present disclosure may have a molecular weight in the range a few glucosamine units of to more than 200,000 Da. In embodiments, the molecular weight can range from 10,000 to 1,000,000 Da, in the range 15,000 to 750,000 Da, or in the range 20,000 to 500,000 Da. In embodiments, the chitosan may range in molecular weight from 300 to 1000 kDa. In embodiments, the chitosan may range in molecular weight from about 300 to 400 kDa, or from about 300 to 500 kDa, or from about 300 to 400 kDa, or from about 300 to 500 kDa, or from about 300 to 600 kDa, or from about 300 to 700 kDa, or from about 300 to 800 kDa, or from about 300 to 900 kDa, or from about 300 to 1000 kDa.

In embodiments, chitosan is one of the polysaccharides that is modified with various groups such as 5β-cholanic acid, linoleic acid, Monomethoxy poly (ethyleneglycol). After modification process, modified chitosan are used for preparation of the composition of the present disclosure. Non-limiting examples of modified chitosan and methods of preparing such modified chitosan are listed in Table 1.

Hydroxyethyl cellulose, 0.2 to 2.5 percent Hypromellose, 0.2 to 2.5 percent Methylcellulose, 0.2 to 2.5 percent, Dextran 70, 0.1 percent, Gelatin, 0.01 percent; polyols liquid: Glycerin, 0.2 to 1 percent, Polyethylene glycol 300, 0.2 to 1 percent, Polyethylene glycol 400, 0.2 to 1 percent, Polysorbate 80, 0.2 to 1 percent, Propylene glycol, 0.2 to 1 percent, Polyvinyl alcohol, 0.1 to 4 percent, Povidone, 0.1 to 2 percent; Lanolin preparations: Anhydrous lanolin, 1 to 10 percent Lanolin, 1 to 10 percent; Oleaginous ingredients: Light mineral oil, Mineral oil, Paraffin, Petrolatum, White ointment, White petrolatum, White wax, Yellow wax; and/or Ophthalmic vasoconstrictors: Ephedrine hydrochloride, 0.123 percent, Naphazoline hydrochloride, 0.01 to 0.03 percent, Phenylephrine hydrochloride, 0.08 to 0.2 percent, Tetrahydrozoline hydrochloride, 0.01 to 0.05 percent.

TABLE 1

| Functional molecules for modification of chitosan | |
|---|---|
| Chitosan | Grafting Agent |
| Glycol chitosan | 5β-Cholanic acid |
| Modification: Glycol chitosan is hydrophobically modified with cholanic acid in methanol/water. To activate the carboxylic acid groups of cholanic acid, equal amounts of 1-ethyl-3-(3-dimethylaminopropyl)-carbodiimide hydrochloride and N-hydroxysuccinimide are added. | |
| Chitosan of 100 mesh | Linoleic acid (LA) |
| Modification: Chitosan is dissolved in aqueous acetic acid solution and diluted of methanol. LA is added to the chitosan solution glucosamine residue of chitosan followed by a dropwise addition of 15 mL of EDC methanol solution (0.07 g/L) while stirring. | |
| chitosan | α-Cyclodextrin |
| Modification: α-CD linked chitosan using 2-O-formylmethyl-α-CD by reductive N-alkylation. | |
| Chitosan | e-Caprolactone |

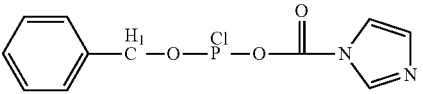

Modification: The PCL-graft-chitosan copolymers are synthesized by coupling the hydroxyl end-groups on preformed PCL chains and the amino groups present on 6-Otriphenylmethyl chitosan and by removing the protective 6-O-triphenylmethyl groups in acidic aqueous solution

| Biomedical grade chitosan | Monomethoxy poly(ethyleneglycol) |
|---|---|
| Modification: Chitosan is completely dissolved in formic acid by stirring and a suitable amount of mPEG is added. After 15 min, enough formaldehyde solution is added to the above mixture and was stirred for 12 h. | |

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and one or more additives. The additives can include components that have been classified by the FDA as Ophthalmic Drug Products for Over-The-Counter Human Use [Title 21, Volume 5]. In embodiments, these additives may be (a) astringents (b) buffering agents (c) demulcents (d) emollients (e) eyewash, eye lotion, irrigating solutions (f) hypertonic agents (g) isotonic agents, and/or (h) vasoconstrictors. In embodiments, these additives may include Zinc sulfate, 0.25 percent; cellulose derivatives: Carboxymethylcellulose sodium, 0.2 to 2.5 percent In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and trehalose, methylcellulose, ethylcellulose, sodium carboxymethylcellulose, hydroxypropylmethylcellulose, sodium hyaluronate, sodium alginate, chitosan, chitosan salts and/or derivatives, polyethylene glycol, glycerin, propylene glycol, Triacetin, N,N-Dimethylacetamide, poly(vinyl pyrrolidone), pyrrolidone, dimethyl sulfoxide, ethanol, N-(-beta-Hydroxyethyl)-lactamide, 1-Methyl-2-pyrrolidinone, triglycerides, monothioglycerol, sorbitol, lecithin, methylparaben, propylparaben, or combinations thereof.

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and a co-solvent. The solubility of the components of the present compositions may be enhanced by a surfactant or other appropriate co-solvent in the composition. Such co-solvents include, but are not limited to, polysorbate 20, polysorbate 60, polysorbate 80, Pluronic F-68, Pluronic F-84 Pluronic P-103, cyclodextrin, and any other suitable agents, or a combination thereof. The co-solvents may be used in any suitable amounts. In embodiments, such co-solvents are used in a concentration of about 5% to about 50% (w/v) of the composition. In embodiments, a solvent that used in a composition of the present disclosure is glycerol.

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and a preservative. Examples of preservatives include an anti-microbial preservative, for example, benzalkonium chloride, thimerosal, chlorhexidine, chlorobutanol, methyl paraben, propyl paraben, phenylethyl alcohol, edetate disodium sorbic acid, Onamer M Polyquat, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, sodium proprionate, and sodium perborate, or any combination(s) thereof.

In embodiments the preservatives may be used in any suitable amounts. For example, the antimicrobial and preservative may be used in an amount about 0.001% by weight-1.0% by weight based on the total weight of composition.

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and a viscosity agent. Any suitable agent that can increase viscosity may be used. Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity agents include, for example polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof. Such agents may be used in any suitable amounts.

The viscosity agents may be used in any suitable amounts. In one aspect, the viscosity agent may be employed at a level in a concentration of from about 0.01% to about 3.0% by weight.

In embodiments, the present disclosure includes a freeze-dried composition for treating dry eye syndrome or for moisturizing and/or repairing non-keratinized surfaces (e.g., dry mouth syndrome, vaginal dryness, diabetic ulcers and other chronic wounds), including non-autologous plasma or serum, and a polymer having a molecular weight of 100 to 1200 kDA, or derivatives thereof, and one or more pH adjusting agents. The pH adjustment agent may be, for example, sodium hydroxide, hydrochloric acid, citric acid, malic acid, tartaric acid, acetic acid, phosphoric acid, maleic acid, glycine, sodium lactate, lactic acid, sodium citrate, ascorbic acid, sodium acetate, acetic acid, sodium bicarbonate, sodium carbonate, carbonic acid, sodium succinate, succinic acid, sodium benzoate, benzoic acid, sodium phosphates, tris(hydroxymethyl)aminomethane, histidine, histidine hydrochloride, or any combination(s) thereof.

Compounds useful as pH regulators include, but are not limited to include boric acid, sodium boric acid, sodium phosphate (including 1, 2 and 3 basic phosphate, such as 1 basic sodium phosphate 1 hydrate, 2 basic sodium phosphate 7 hydrate and mixtures thereof). Any other proper buffers can be used to stabilize the pH level of the ophthalmic liquid medicine by conferring physiological pH approved for ophthalmic liquid medicines. Since said buffers are just examples and these buffers are well known in ophthalmologic field, a person skilled in the art can choose proper buffers that can be used for the composition of the present disclosure.

In embodiments, the compositions of the present disclosure is formulated as a solution, a suspension, a semi-solid gel, a gel, an emulsion, semi-liquid, an ointment, a cream, foam gel, or a controlled-release/sustain-release vehicle. For example, the composition may be in the form of a contact lens solution, eyewash, eye drop, eye gel, eye ointment, and the like.

In embodiments, the freeze-dried composition is reconstituted with a reconstitution fluid. The reconstitution fluid may refer to any solvent described herein. In embodiments, water or a saline solution may be used, any additives may be included into the reconstitution fluid, and artificial or non-autologous plasma or serum may also be used as a reconstitution fluid. In embodiments, the solvents used for the reconstitution fluid is sterile.

In embodiments, the reconstitution fluid includes an additive (e.g., ascorbic acid, glycine, or a combination thereof). In embodiments, an additive included in the reconstitution fluid has been classified by the FDA as Ophthalmic Drug Products for Over-The-Counter Human Use [Title 21, Volume 5]. In embodiments, these additives can be (a) astringents (b) buffering agents (c) demulcents (d) emollients (e) eyewash, eye lotion, irrigating solutions (f) hypertonic agents (g) isotonic agents, and/or (h) vasoconstrictors. In embodiments, these additives may include Zinc sulfate, 0.25 percent; cellulose derivatives: Carboxymethylcellulose sodium, 0.2 to 2.5 percent Hydroxyethyl cellulose, 0.2 to 2.5 percent Hypromellose, 0.2 to 2.5 percent Methylcellulose, 0.2 to 2.5 percent, Dextran 70, 0.1 percent, Gelatin, 0.01 percent; polyols liquid: Glycerin, 0.2 to 1 percent, Polyethylene glycol 300, 0.2 to 1 percent, Polyethylene glycol 400, 0.2 to 1 percent, Polysorbate 80, 0.2 to 1 percent, Propylene glycol, 0.2 to 1 percent, Polyvinyl alcohol, 0.1 to 4 percent, Povidone, 0.1 to 2 percent; Lanolin preparations: Anhydrous lanolin, 1 to 10 percent Lanolin, 1 to 10 percent; Oleaginous ingredients: Light mineral oil, Mineral oil, Paraffin, Petrolatum, White ointment, White petrolatum, White wax, Yellow wax; and/or Ophthalmic vasoconstrictors: Ephedrine hydrochloride, 0.123 percent, Naphazoline hydrochloride, 0.01 to 0.03 percent, Phenylephrine hydrochloride, 0.08 to 0.2 percent, Tetrahydrozoline hydrochloride, 0.01 to 0.05 percent.

The freeze-dried composition of the disclosure can be reconstituted, for example, under sterile condition, with a solvent, such as water or a saline solution (e.g. 0.9% w/v sodium chloride for injection) prior to use, thereby generating a reconstituted liquid or semi-liquid composition. In embodiments, freeze-dried serum and plasma are reconstituted in sterile water or other comparable solvents and approved additives to allow the ability to titrate pH, osmolarity, surface tension, and viscosity. Because $CO_2$ is removed during the freeze dried process which results in an alkaline pH (8.2), the sterile water contains additives including glycine (pH 2.4) and ascorbic acid to obtain a final pH of approximately 7.4. In some embodiments, plasma or serum is used as a reconstitution fluid for treatment of dry eye syndrome, or other ophthalmic diseases because serum contains many key components as does plasma, which include growth factors, vitamins, minerals and natural lubricants such as lipids. In embodiments, the reconstituted composition is tested in an animal model. For example, the composition including non-autologous plasma or serum and a polymer as described herein can be used in an animal model to determine the efficacy, toxicity, or side effects of treatment with said composition.

Pharmaceutical Compositions and Formulations

The disclosure also provides pharmaceutical compositions including non-autologous serum and a polymer. In some embodiments, the pharmaceutical composition comprises non-autologous serum and a polymer, and at least one pharmaceutically acceptable excipient or carrier. Preferably, the amount is a therapeutically effective amount.

In embodiments the pharmaceutical composition may include a pharmaceutically acceptable carrier. The type of carrier can be selected based upon the intended route of administration. Pharmaceutically acceptable carriers include sterile aqueous solutions (e.g., sterile water) or dispersions and sterile powders for the extemporaneous preparation of sterile topical solutions or dispersions. The use of such media and agents for pharmaceutically active substances is well known in the art. Except insofar as any conventional media or agent is incompatible with the composition (e.g., freeze-dried plasma or serum), use thereof in the freeze-dried compositions for the disclosure is contemplated.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In embodiments, the pharmaceutical composition may include a pharmaceutically acceptable excipient, which may refer to an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof. In embodiments, the excipients may be selected from sucrose and trehalose.

In embodiments, the pharmaceutical composition is in the form of a liquid or solution formulation suitable for topical administration as a drop, particularly as an ophthalmic drop. In embodiments, the pharmaceutical composition is in the form of a solid composition such as a powder suitable for reconstitution into a liquid form. In embodiments, the pharmaceutical composition is in the form of a solid or semi-solid composition such as an ointment, paste, cream, lotion, or gel. In embodiments, the pharmaceutical composition is in the form of a cohesive solid material in a defined shape, such as a wafer or disc (alternatively, a lens, pessary, or denture) which may be used as, or in combination with a dressing, e.g., a wound dressing. In embodiments, the pharmaceutical composition is formulated for topical administration by application to a non-keratinized surface such as an ophthalmic, oral, vaginal, buccal, sublingual, or rectal surface. For example, a pharmaceutical composition of the invention may be in the form of an aqueous solution in the form of eye drops, or a solid in the form of a disc, wafer, or lens, e.g., a contact lens, a pessary, a wound dressing, or denture. In embodiments, the pharmaceutical composition is sterile.

Methods of Treatment or Use

In one aspect, the present disclosure provides a method of treating an ophthalmic disease of the anterior segment (e.g., dry eye syndrome) in a subject in need thereof, the method including administering to an eye of the subject a reconstituted freeze-dried composition including non-autologous plasma or serum and a polymer, in an amount to treat dry eye syndrome in the subject. In embodiments, the polymer or derivatives thereof has a molecular weight of 100 to 1200 kDA.

In one aspect, the present disclosure provides a method of moisturizing and/or repairing non-keratinized surfaces (e.g., dry mouth syndrome, vaginal dryness, diabetic ulcers and other chronic wounds) in or on the body of a subject. The method of moisturizing and/or repairing non-keratinized surfaces (e.g., dry mouth syndrome, vaginal dryness, diabetic ulcers and other chronic wounds) includes, e.g., delivering a composition of the present disclosure with the therapeutic agent delivery device (100) of the present disclosure to a non-keratinized surface of a subject in need thereof.

In embodiments, the moisturizing and/or repairing non-keratinized surfaces includes treatment of dry mouth syndrome, vaginal dryness, diabetic ulcers, and/or chronic wounds.

In one aspect, the present disclosure provides a method of treating an ophthalmic disease of the anterior segment (e.g., dry eye syndrome) in a subject in need thereof, the method including administering to an eye of the subject a reconstituted freeze-dried composition including non-autologous plasma or serum and a polymer having a molecular weight of 100 to 1200 kDA and a formula including of Formula 1: $[[R_1]m-L-[R_2]n]p$, or derivatives thereof, where $R_1$ and $R_2$ are units of the polymer, m is an integer from 1-10,000, n is an integer from 1-10,000, and p is an integer from 10-10,000, L is a bond. In some embodiments, "m" and "n" of Formula I is 1.

In one aspect, the present disclosure provides a method of increasing ocular surface retention of an ophthalmic composition, the method including administering to an eye of the subject a composition including non-autologous plasma or serum and a polymer having a molecular weight of 100 to 1200 kDA and/or a formula including of Formula 1: $[[R_1]m-L-[R_2]n]p$, or derivatives thereof, where $R_1$ and $R_2$ are units of the polymer, m is an integer from 1-10,000, n is an integer from 1-10,000, and p is an integer from 10-10,000, L is a bond. In some embodiments, "m" and "n" of Formula I is 1.

In one aspect, the present disclosure provides a method of moisturizing and/or repairing non-keratinized surfaces (e.g., dry mouth syndrome, vaginal dryness, diabetic ulcers and other chronic wounds) in a subject in need thereof, the method including administering to the non-keratinized surface a composition including reconstituted freeze-dried composition including non-autologous plasma or serum and a polymer having a molecular weight of 100 to 1200 kDA and/or a formula including of Formula 1: $[[R_1]m-L-[R_2]n]p$, or derivatives thereof, where $R_1$ and $R_2$ are units of the polymer, m is an integer from 1-10,000, n is an integer from 1-10,000, and p is an integer from 10-10,000, L is a bond. In some embodiments, "m" and "n" of Formula I is 1.

The freeze-dried composition of the present disclosure is reconstituted with a reconstitution fluid. The reconstitution fluid can be any aqueous solvent. For example, distilled or sterile water or a saline solution (e.g. 0.9% w/v sodium chloride for injection). In embodiments, the reconstitution fluid includes additives (i.e., glycine or ascorbic acid, or chitosan, alginate, and gelatin). In some embodiments, the reconstitution fluid includes plasma or serum, or components thereof. In embodiments, the solvents used for the reconstitution fluid may be sterile.

In embodiments, the present disclosure includes a method of treating dry eye syndrome or a method of moisturizing and/or repairing non-keratinized surfaces (e.g., dry mouth syndrome, vaginal dryness, diabetic ulcers and other chronic wounds) in a subject in need thereof, the method including administering to an eye or a non-keratinized surface of the subject, respectively, a reconstituted freeze-dried composition including non-autologous plasma or serum, and chitosan or derivatives thereof. In embodiments, the present disclosure includes a method of treating dry eye syndrome or a method of moisturizing and/or repairing non-keratinized surfaces (e.g., dry mouth syndrome, vaginal dryness, diabetic ulcers and other chronic wounds) in a subject in need thereof, the method including administering to an eye or a non-keratinized surface of the subject, respectively, a reconstituted freeze-dried composition including mammalian (e.g., human) umbilical cord plasma and chitosan or derivatives thereof. In embodiments, the present disclosure includes a method of treating dry eye syndrome or a method of moisturizing and/or repairing non-keratinized surfaces (e.g., dry mouth syndrome, vaginal dryness, diabetic ulcers and other chronic wounds) in a subject in need thereof, the method including administering to an eye or a non-keratinized surface of the subject, respectively, a reconstituted freeze-dried composition including mammalian (e.g., human) umbilical cord serum and chitosan or derivatives thereof.

Treatment of Types of Dry Eye Syndrome

In embodiments, the method of treating dry eye syndrome includes treating aqueous tear-deficient dry eye, which is a disorder in which the lacrimal glands fail to produce enough of the watery component of tears to maintain a healthy eye surface, with a composition of the present disclosure. In embodiments, the method of treating dry eye syndrome includes treating evaporative dry eye, which may result from inflammation of the meibomian glands (these glands make the lipid or oily part of tears that slows evaporation and keeps the tears stable), also located in the eyelids, with a composition of the present disclosure.

In embodiments, the method of treating dry eye syndrome includes treating dry eye associated with or resulting from treating inflammation of the surface of the eye, the lacrimal gland, or the conjunctiva; dry eye associated with any disease process that alters the components of the tears; dry eye associated with an increase in the surface of the eye, as in thyroid disease when the eye protrudes forward; and/or dry eye associated with a cosmetic surgery, for example, if the eyelids are opened too widely during surgery.

In embodiments, the method of treating dry eye syndrome includes ameliorating a symptom of dry eye syndrome, including: stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses; decreased tolerance of reading, working on the computer, or any activity that requires sustained visual attention; and/or eye fatigue.

In embodiments, the method of treating dry eye syndrome includes treating or ameliorating a symptom associated of dry eye syndrome in a subject exposed to a risk factor of temporary or chronic dry eye such as: side effect of some medications, including antihistamines, nasal decongestants, tranquilizers, certain blood pressure medicines, Parkinson's medications, birth control pills and anti-depressants; skin disease on or around the eyelids can result in dry eye; diseases of the glands in the eyelids, such as meibomian gland dysfunction; pregnancy; hormone replacement therapy in women (women taking only estrogen are 70 percent more likely to experience dry eye, whereas those taking estrogen and progesterone have a 30 percent increased risk of developing dry eye); refractive surgery known as LASIK; chemical and thermal burns that scar the membrane lining the eyelids and covering the eye; allergies; infrequent blinking, associated with staring at computer or video screens; both excessive and insufficient dosages of vitamins that can contribute to dry eye; homeopathic remedies that may have an adverse impact on a dry eye condition; loss of sensation in the cornea from long-term contact lens wear can lead to dry eye; dry eye can be associated with immune system disorders such as Sjögren's syndrome, lupus, and rheumatoid arthritis (Sjögren's leads to inflammation and dryness of the mouth, eyes, and other mucous membranes. It can also affect other organs, including the kidneys, lungs and blood vessels); dry eye can be a symptom of chronic inflammation of the conjunctiva, the membrane lining the eyelid and covering the front part of the eye, or the lacrimal gland (chronic conjunctivitis can be caused by certain eye diseases, infection, exposure to irritants such as chemical fumes and tobacco smoke, or drafts from air conditioning or heating); if the surface area of the eye is increased, as in thyroid disease when the eye protrudes forward or after cosmetic surgery if the eyelids are opened too widely, dry eye can result; dry eye may occur from exposure keratitis, in which the eyelids do not close completely during sleep.

In embodiments, the disclosure provides a method of treating dry eye syndrome in a subject in need of such treatment by increasing the tear film breakup time in the eyes of the subject. Break-up of the tear film is initiated at points where the surface of the corneal epithelium is irregular and where epithelial cells have been damaged or have lost their wettability. Active components in the freeze-dried plasma or serum compositions described here promote the health of the corneal epithelium, especially with improved stratification and differentiation of corneal epithelial cells that produce a surface glycocalyx. In embodiments, the disclosure also provides methods of reducing, ameliorating, or preventing damage to the corneal epithelium, for example as indicated by the uptake of Rose Bengal dye.

Co-Administration—with Other Drugs/Treatment Methods

In embodiments, the method of treating dry eye syndrome can be managed as an ongoing condition. In embodiments, whether there is a disease that is the underlying cause of the dry eye (such as Sjögren's syndrome or lacrimal and meibomian gland dysfunction) is determined. In embodiments, if there is an underlying disease, that disease is concurrently treated.

In embodiments, the method includes treating dry eye with a composition of the present disclosure in combination with cyclosporine (cyclosporine is an anti-inflammatory medication available to treat dry eye). In embodiments, the method of treating dry eye syndrome includes administering a composition including non-autologous plasma or serum and a polymer having molecular weight of 100 to 1200 kDA, or derivatives thereof, in combination with cyclosporine. In embodiments, the method includes administering a composition of the present disclosure concurrently, sequentially, simultaneously with cyclosporine. In embodiments, the method of treating dry eye syndrome includes administering a composition including non-autologous plasma or serum and a polymer having molecular weight of 100 to 1200 kDA, or derivatives thereof, in combination with a corticosteroid eye drop for decreasing inflammation. In embodiments, the method includes administering a composition of the present disclosure concurrently, sequentially, simultaneously with a corticosteroid. In embodiments, the method includes administering a composition of the present disclosure concurrently, sequentially, simultaneously with cyclosporine and a corticosteroid.

In embodiments, the method of treating dry eye syndrome includes administering a composition of the present disclosure to a subject wearing contact lens.

In embodiments, the method of treating dry eye syndrome includes administering a composition of the present disclosure to a subject in whom another method has been performed to treat dry eye. For example, in one such method a physician has plugged the drainage holes or punctum, which are small circular openings at the inner corners of the eyelids where tears drain from the eye into the nose, before administering a composition of the present disclosure. In embodiments, tear duct plugs, also called punctal plugs, has been inserted by an eye care professional (Punctal plugs are made of silicone or collagen, are reversible, and are a temporary measure). In severe cases, permanent plugs have been inserted before administering a composition of the present disclosure.

In additional embodiments, a simple surgery, called punctal cautery, has been performed permanently close the drainage holes, before administering a composition of the present disclosure. The procedure helps keep the limited volume of tears on the eye for a longer period of time.

In embodiments, the method of treating dry eye syndrome or the method of moisturizing and/or repairing non-keratinized surfaces (e.g., dry mouth syndrome, vaginal dryness, diabetic ulcers and other chronic wounds) includes administering a composition of the present disclosure to a subject with dry eye or a non-keratinized surface, and the subject is on supplements or dietary sources (such as salmon) of omega-3 fatty acids (especially DHA and EPA) for decreasing symptoms of irritation associated with dry eye or a dry non-keratinized surface.

In embodiments, the method of moisturizing and/or repairing non-keratinized surfaces (e.g., dry mouth syndrome, vaginal dryness, diabetic ulcers and other chronic wounds) can be managed as an ongoing condition. In embodiments, the disease that is the underlying cause is determined. In embodiments, if there is an underlying disease, that disease is concurrently treated.

In embodiments, the method of moisturizing and/or repairing non-keratinized surfaces (e.g., dry mouth syndrome, vaginal dryness, diabetic ulcers and other chronic wounds) includes administering a composition including non-autologous plasma or serum and a polymer having molecular weight of 100 to 1200 kDA, or derivatives thereof, in combination with any suitable lubricating and/or moisturizing agents. Exemplary vaginal moisturizers include, but are not limited to, Replens®, K-Y Liquibeads®, Lubrin®, Astroglide Silken Secret® and Vitamin E gel. Examples of oral moisturizes (i.e. for dry mouth) may include, but are not limited to, artificial saliva products, saliva stimulants, Salese Soothing®, Orajel®, and Eucerin® cream. Exemplary moisturizers for diabetic ulcers and/or chronic wounds may include any saline or similar dressings that provide a moist environment, TriDerma® MD Ulcer Healing Cream, or Neoteric Diabetic Healing Cream®.

In embodiments, the method of moisturizing and/or repairing non-keratinized surfaces (e.g., dry mouth syndrome, vaginal dryness, diabetic ulcers and other chronic wounds) includes administering a composition including non-autologous plasma or serum and a polymer having molecular weight of 100 to 1200 kDA, or derivatives thereof, in combination with any suitable lubricating and/or moisturizing agents. In embodiments, the method includes administering a composition of the present disclosure concurrently, sequentially, and simultaneously with any suitable lubricating and/or moisturizing agents. In embodiments, the method includes administering a composition of the present disclosure concurrently, sequentially, and simultaneously with cyclosporine and any suitable lubricating and/or moisturizing agents.

In embodiments, the method of moisturizing and/or repairing non-keratinized surfaces (e.g., dry mouth syndrome, vaginal dryness, diabetic ulcers and other chronic wounds) includes administering a composition of the present disclosure to a subject in whom another method has been performed to moisturize and/or repair non-keratinized surfaces (e.g., dry mouth syndrome, vaginal dryness, diabetic ulcers and other chronic wounds).

In embodiments, the method of moisturizing and/or repairing non-keratinized surfaces (e.g., dry mouth syndrome, vaginal dryness, diabetic ulcers and other chronic wounds) includes administering a composition of the present disclosure to a subject with dry eye or a non-keratinized surface, and the subject is on supplements or dietary sources (such as salmon) of omega-3 fatty acids (especially DHA and EPA) for decreasing symptoms of irritation associated with a dry non-keratinized surface.

Dosage Regimen

In embodiments, the method of treating dry eye syndrome or moisturizing and/or repairing non-keratinized surfaces (e.g., dry mouth syndrome, vaginal dryness, diabetic ulcers and other chronic wounds) includes administering a composition of non-autologous plasma or serum to a subject in any suitable or therapeutically effective amount, e.g., from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight, or any range in between, of the composition.

In embodiments, a method of treating an ophthalmic disease of the anterior segment (e.g., dry eye syndrome) or a method of moisturizing and/or repairing non-keratinized surfaces (e.g., dry mouth syndrome, vaginal dryness, diabetic ulcers and other chronic wounds) in a subject in need thereof, includes administering to an eye or a non-keratinized surface of the subject, respectively, a reconstituted freeze-dried composition including non-autologous plasma or serum and a polymer (e.g., chitosans, alginates, or gelatins). In embodiments, the amount of polymer in the composition is at a concentration of from about 0.025% to about 2.0% by weight of the composition. The polymer can be present at about 0.025, about 0.05, about 0.1, about 0.2, about 0.3, about 0.4, about 0.5, about 1.0, and about 2.0 percent by weight or any amount in between these amounts of the composition. In an embodiment, the polymer may be in a concentration of about 0.05% (w/v) to about 1.0% (w/v) of the composition.

In embodiments, a method of treating an ophthalmic disease of the anterior segment (e.g., dry eye syndrome) or a method of moisturizing and/or repairing non-keratinized surfaces (e.g., dry mouth syndrome, vaginal dryness, diabetic ulcers and other chronic wounds) in a subject in need thereof, includes administering to an eye or a non-keratinized surface of the subject, respectively, a reconstituted freeze-dried composition including non-autologous plasma or serum and a polymer, formulated in the form of a solution, a suspension, a semi-solid gel, a gel, an emulsion, semi-liquid, an ointment, a cream, foam gel, or a controlled-release/sustain-release vehicle. For example, the composition may be in the form of a contact lens solution, eyewash, eye drop, eye gel, eye ointment, and the like.

In embodiments, a method of treating an ophthalmic disease of the anterior segment (e.g., dry eye syndrome) or a method of moisturizing and/or repairing non-keratinized surfaces (e.g., dry mouth syndrome, vaginal dryness, diabetic ulcers and other chronic wounds) in a subject in need thereof includes topically administering to an eye or a non-keratinized surface of the subject, respectively, a reconstituted freeze-dried composition including non-autologous plasma or serum and a polymer. In embodiments, the reconstituted composition (e.g., ophthalmic composition) is administered in the form of eyedrops. In embodiments the reconstituted composition (e.g., ophthalmic composition) may be formulated as a solution, suspension, semi-liquid, semi-solid gel, gel, emulsion, ointment, or cream.

In embodiments, the reconstituted composition (e.g., ophthalmic composition) may be administered topically to an eye or a non-keratinized surface in a dose range from about 0.001 mg to about 100 mg per eye or desired non-keratinized surface area, respectively. In some embodiments, the dosage for one eye or a desired area of a non-keratinized surface may be about one drop of reconstituted composition which may correspond to about 50 µL to about 150 µL of reconstituted composition.

In embodiments, the reconstituted composition may be administered topically to an eye or a non-keratinized surface by placing one to two drops or more in each eye or a desired non-keratinized surface area, respectively, 1 to 24 times daily. For example, the composition may be applied, 1, 2, 3, 4, 8, 12, 18 or 24 times a day, or more. In an embodiment, the composition may be applied by placing one or two drops in each eye or a desired area of a non-keratinized surface, respectively, once or twice daily.

In embodiments, the moisturizing of a mucosal surface increasing the moisture content of the surface by about 5% to about 100% (compared to physiologically normal non-keratinized surface). In embodiments, repairing of a mucosal surface increasing the moisture content of the surface by about 5% to about 100% (compared to physiologically normal non-keratinized surface) and healing a wound (e.g., abrasions, cuts, ulcers, tissue damages).

Delivery Device

In one aspect, the current disclosure provides a therapeutic agent delivery device (100) which incorporates the above compositional elements (e.g., the freeze-dried non-autologous plasma or serum and polymer, and a reconstitution fluid) in one or more compartments/chambers (101 and/or 102). The delivery device (100) includes two-chambers (Chambers A (101) and B (102)) Chamber A (101) is configured to contain freeze-dried, sterile, freeze-dried plasma or serum Chamber B (102) is configured to contain aqueous reconstitution fluid including pH adjustment elements (e.g. ascorbic acid) and/or other additives as protectants (e.g. chitosan, alginate, gelatin). A non-permeable membrane (103) between Chamber A (101) and Chamber B (102) is configured to separate chamber A (101) and chamber B (102).

The non-permeable membrane (103) can be broken on-demand by a user of the delivery device (100), in order to mix the lyophilized (or freeze-dried) plasma or serum and the reconstitution fluid. The mechanism of membrane disruption can occur by several means: one example includes a digital mechanism, by which the user presses a button on the delivery device (100), and an electromechanical signal causes the membrane to become permeable; in another example, the delivery device (100) can be agitated or twisted by the user in order to disrupt the membrane and allow mixing of components in Chamber A (101) and Chamber B (102).

At the distal end of the delivery device (100) is a dropper (106), which is configured to dispense the resulting fluid upon mixing of chamber A (101) and chamber B (102); the dropping of droplets may occur by the user squeezing the body of the delivery device (100). This delivery device (100)

can be stored at room temperature as the freeze-dried serum or plasma does not degrade at the speed it would in a wet state.

The therapeutic agent delivery device (100) is covered or surrounded by a chamber casing (104). The ophthalmic therapeutic agent delivery device (100) includes a dropper casing (105).

The therapeutic agent delivery device (100) has longitudinal dimension of the device is about 5 cm-10 cm. The ophthalmic therapeutic agent delivery device (100) of claim 31, wherein the horizontal dimension of the device is about 1 cm-4 cm.

In embodiments, the therapeutic agent delivery device (100) of the present disclosure is used for delivering a composition. For example, the therapeutic agent delivery device (100) includes a freeze-dried composition in chamber A (101) and upon reconstitution with the fluid in chamber B (102) is delivered to the eye of a subject through the dropper (106) for treating dry eye syndrome.

In embodiments, the therapeutic agent delivery device (100) of the present disclosure includes a freeze-dried composition in the first chamber (101) and a reconstitution fluid in the second chamber (102), and upon reconstitution, the reconstituted composition is delivered to a subject.

In embodiments, the therapeutic agent delivery device (100) of the present disclosure includes the reconstituted composition which is for treating dry eye syndrome, or moisturizing and/or repairing a non-keratinized surface.

EXAMPLES

Example 1: Serum and Plasma Collection

Voluntary pedigree donors are kept in either single donor lots or as ABO type specific minipool (<11 donors) lots as a precaution against potential infectious agents including prion risk. Both serum and plasma are from whole blood collections. Human umbilical cord serum and plasma are from voluntary pedigree mothers during vaginal or cesarean section delivery.

Blood is collected at FDA licensed, US collection centers, and total quality system and good manufacturing practice (GMP) facilities are used. To ensure safety, the product undergoes two mandatory phases, incorporating safety measures inherent in FDA licensed plasma.

Example 2: Serum and Plasma Pathogen Reduction

Phase 1 Pathogen Reduction: Pedigree Donors and Quarantine

Voluntary pedigree donors undergo physical examination and screening to detect the presence of infection in accordance with FDA guidelines. Exemplary infections tested for include, for example, *Trypanosoma cruzi*, Hepatitis B and C virus, Human Immunodeficiency Virus Types 1 and 2 (HIV-1 and HIV-2), *Treponema pallidum* (TPHA), Toxoplasmosis (TOXO), Cytomegalovirus (CMV), Human T-Lymphotropic virus (HTLV-I/II) and West Nile virus (WNV). Multiplex nucleic acid testing is performed, on for example, HIV, Hepatitis B Virus (HBV), and Hepatitis C Virus-nucleic acid testing (HCV-NAT). A hemovigilance program is utilized. Donor Serum and plasma is quarantined frozen before undergoing processing until repeat donor examinations and testing again at 4 months ensures no infections are detected.

Phase 2 Pathogen Reduction

Serum and plasma undergoes pathogen reduction after completion of phase 1, using the Intercept Blood System. The system uses Amotosalen HCl, a synthetic psoralen, or other similar method. Typically a photoactive solvent/detergent is mixed into the serum or plasma and exposed to ultraviolet light. With Amotosalen HCl, photoactivation occurs when the mixture is illuminated with UVA treatment at 3 J/cm². Once treated, the serum and plasma are stored and frozen at minus 70° C. for future freezing drying.
Phase 3: Pathogen Reduction (Optional)

Gamma irradiation between 10 and 50 kGy is performed to the freeze-dried serum and plasma at 4° C. Ascorbate is added as a protectant for plasma proteins against gamma irradiation and for pH balance.

Example 3: Freeze-Drying of Serum and Plasma

Samples are thawed and incubated at 23° C. for 1 hour, and centrifuged at 3,000 g for 10 minutes with retention of the resulting supernatant. 300 mL aliquots of the serum/plasma supernatant for lyophilization are placed in a sterile 1 L cylindrical Pyrex (10 cm diameter, 25 cm height) vessel, and frozen in an even layer on the bottom and side of the container by slow rotation in isopropanol dry-ice slurry.

The resulting frozen serum/plasma is then freeze dried for 48 hours at 8° C. in a Virus Unitop 600 SL lyophilizer or other comparable unit.

Additives in measured amounts are used for pH balance and as a protectant for serum/plasma proteins against gamma irradiation. The freeze-dried serum/plasma can be stored at or below room temperature (25° C.). Temperatures of 50° C. or greater for storage because of risk of degradation of plasma/serum proteins.

Example 4: Reconstitution of Freeze-Dried Plasma/Serum

Freeze-dried serum and plasma are reconstituted in sterile water (i.e. in 300 mL aliquots), and optionally along with other comparable solvents and approved additives to allow the ability to titrate pH, osmolarity, surface tension, and viscosity. The sterile water contains additives including glycine (pH 2.4) and ascorbic acid to obtain a final pH 7.4 and fast reconstitution (~5 min in reconstitution fluid) before use.

Example 5: Freeze-Dried Samples of Biopolymers Mixed with Human Plasma or Serum Upon mixing chitosan or hydrophobically-modified (hm) chitosan (each 2 wt % solutions in 0.2 M AcOH) with human plasma or human serum, liquid mixtures were obtained. The solutions were poured into weigh boats, which were freeze-dried to remove water. The resulting structures were wafers with dimensions of 50 mm×50 mm×4 mm which were beige to a yellowish color, largely dominated by the color of the plasma or serum. The amount of chitosan was about 25 wt % based on the final dry weight of the composition, and the amount of the plasma or serum components was about 75 wt %.

Mixtures were made in a 50/50 w/w ratio of biopolymer (e.g., chitosan or hm-chitosan) to blood component (plasma or serum); 9.7 g biopolymer to 9.7 g of blood component, thus the final weight percent of chitosan in the solution mixture prior to freeze-drying was about 1%. In control samples, only serum or plasma was present, there was no chitosan in these samples. Samples were freeze-dried for 36 h at −20° C., and then for 12 h at +10° C. at an average vacuum of 100 μbar. Exemplary results are shown in Table 2 below.

TABLE 2

Properties of samples of biopolymers mixed with human plasma or serum

| Sample # | Components | Color | Consistency | Integrity |
|---|---|---|---|---|
| 1 | Serum only | beige/yellow | Homogeneous with cracks on surface of wafer | Easily friable |
| 2 | Plasma only | beige/yellow | Homogeneous with cracks on surface of wafer | Easily friable |
| 3 | Serum + Chitosan | beige/yellow | Homogeneous | Moderately cohesive; cracks with low pressure |
| 4 | Plasma + Chitosan | beige/yellow | Homogeneous | Moderately cohesive; cracks with low pressure |
| 5 | Serum + hm-Chitosan | beige/yellow | Homogeneous | Cohesive; cracks with forceful pressure |
| 6 | Plasma + hm-chitosan | beige/yellow | Homogeneous with cracks on surface of wafer | Moderately cohesive; cracks with low pressure |

The results indicated that to apply serum as a solid dressing, chitosan or hm-chitosan could be pre-mixed with the serum which thereby created a cohesive sponge-like solid. Without the biopolymer, the serum on its own was much too friable to apply to an anatomical surface.

Additionally, the chitosan and hm-chitosan formed a less cohesive dressing with plasma than with the serum. This may be related to an interaction between the chitosan and clotting proteins present in the plasma, but not present in the serum.

Example 6: Synthesis of Hydrophobically-Modified Chitosan

Hydrophobically-modified (hm) chitosan was synthesized by addition of palmitic anhydride (0.1 g; TCI America) dissolved in 20 mL EtOH at 70° C. to Chitosan (2.0 g; Chitoclear hqg 400, Primex (Iceland)) dissolved in 200 mL of a 50/50 v/v mixture of 0.2 M AcOH in water and EtOH at 70° C. The reaction was performed under continuous stirring for 1 hour. The product was precipitated by dropwise addition of 1.0M NaOH. Finally, the resulting precipitate was washed with 100 mL of EtOH, and dried under vacuum overnight. The dried pulp was pulverized into powder, which was then redissolved in 0.2M AcOH in water as described earlier in this section for mixture with blood components.

Example 7: Mixing Serum with Chitosans of Varying Molecular Weights

Upon mixing chitosan (each 2 wt % solutions in 0.2 M AcOH) with human serum, liquid mixtures were obtained of varying viscosities and mucoadhesive strengths. Chitosans (low molecular weight (~100 kDa), medium molecular weight (~250 kDa) and high molecular weight (~400 kDa)) were obtained from Sigma. Zero-shear viscosities were measured with an AR2000 Stress-controlled rheometer under steady-state flow (n=3). Mucoadhesion measurements were performed using a TA-XT Texture Analyzer (Stable Micro Systems) equipped with a load cell of 1 kg (n=3). A/MUC measuring system (mucoadhesion test ring) consisting of a ring in which the biological support can be fixed and a cylinder probe with a diameter of 1 cm were used. In this study, mucin dispersion (mucin from porcine stomach, Type II, Sigma-Aldrich, Germany) was used instead of a biological support. A filter paper disc was wetted with 10 mL of mucin dispersion in phosphate buffer (8%, m/m, pH 6.4). 20 mg of each sample was applied to the cylinder probe. The sample and biologic substrate were put in contact with a preload of 6000 mN for 3 min. The cylinder probe was moved upwards at a predetermined speed of 2.5 mm min$^{-1}$ to separate the mucoadhesive interface (mucin-sample). Exemplary results are shown in Table 3 below.

TABLE 3

Properties of samples of serum mixed with chitosans of varying molecular weights

| Sample # | Components | Viscosity (mPa · s) | Mucoadhesiveness (N mm) |
|---|---|---|---|
| 1 | Serum only | 1.75 ± 0.06 | 0.001 ± 0.00012 |
| 3 | Serum + Chitosan (low molecular weight) | 122 ± 5 | 0.011 ± 0.001 |
| 4 | Serum + Chitosan (medium molecular weight) | 276 ± 16 | 0.021 ± 0.005 |
| 5 | Serum + Chitosan (high molecular weight) | 1,257 ± 112 | 0.075 ± 0.007 |

The data showed a clear increase in viscosity and mucoadhesiveness as the molecular weight of the chitosan increased. These variables are important to the application of the formulation to the eye for optimized therapeutic effect via bioavailability of the serum.

As described in detail above, the molecular structure of chitosan enables its properties to be modified. The amount of chitosan added to the freeze-dried plasma or serum composition can also be adjusted. The viscosity and the mucoadhesive nature of the freeze-dried plasma or serum composition can be adjusted, i.e., to range from a liquid form (i.e., that could be placed in a bottle as drop), to a film that can be molded into any shape and be used as a patch and possible even a contact lens. Between the liquid form and the film form there can be made forms that resemble both gels and ointments.

Depending on the traumatized non-keratinized epithelial surface being treated, one form may be more suitable then the other. For example for dry eye a drop may be the most commonly used or preferred form. For cases of very severe dry eye, a gel and ointment form may be more suitable. Additionally, a contact lens made out of a film that slowly biodegrades and releases the serum/plasmas bioactive proteins over time may be better suited for cases of the most severely traumatized corneal epithelium.

Example 8: Determination of the Glass Transition Temperature (Tg') and Collapse Temperature of Sucrose Formulation Containing Pooled Human Serum and Human Plasma Materials Supplied and Preparation Pooled human serum and pooled human plasma with 4% (w/v) sodium citrate were used. 40 µL (240 mg) of serum or plasma sample was mixed with 20 µL of 15% (w/v) sucrose (0.22 µm filtered) to yield 60 µL of formulation (i.e., 40 mg/mL total protein in 5% (w/v) sucrose).

Methods

Differential Scanning calorimetry (DSC): A TA Q1000 Modulated DSC equipped with a RCS (refrigerated cooling system) (TA Instruments, New Castle, Del.) was used to determine the glass transition temperature of the sucrose formulations containing serum and plasma samples. A 10 µl sample was placed into an aluminum pan and hermetically sealed. The mass of the sample, the pan, and the reference pan were used to determine differences in heat flow between the sample and reference (an empty pan). Nitrogen (NT 3500) was used as the purge gas with a flow rate of 50 mL/min. Samples were run in a conventional DSC mode, with −10° C./min cooling rate from 20° C. to −60° C., isothermal at −60° C. for 30 minutes and a scan rate of 2° C./min during ramp up from −70° C. to +20° C.

Freeze-Drying Microscopy (FDM): Traditional low temperature freeze drying microscopy (FDM) was performed using a temperature and pressure controlled FDCS 196 stage (Linkam, Tadworth, Surrey, UK) and an optical microscope (Olympus BH-2, Tokyo, Japan) equipped with a color video camera (QImaging, Surrey, BC, Canada). A 15 mm round glass cover slide was placed on the freezing stage block, over a drop of silicon immersion oil which improves the contact and heat transfer from the block to the glass. Then 4.5 uL of sample was pipetted onto the 15 mm glass cover slide as a drop. The sample was subsequently covered with a 9 mm glass cover slide to spread the sample volume evenly between the two glass cover slides. The sample was cooled to −50° C. at 10° C./min and equilibrated for 30 minutes at 200 mTorr vacuum. The sample block was then carefully heated to −5° C. at a rate of at 1.0° C./min. Images were captured after every 1° C. rise in temperature using a digital camera system and were analyzed qualitatively to determine the structural changes in the sample. The onset of structural changes indicates collapse.

Results

Figure 2A:
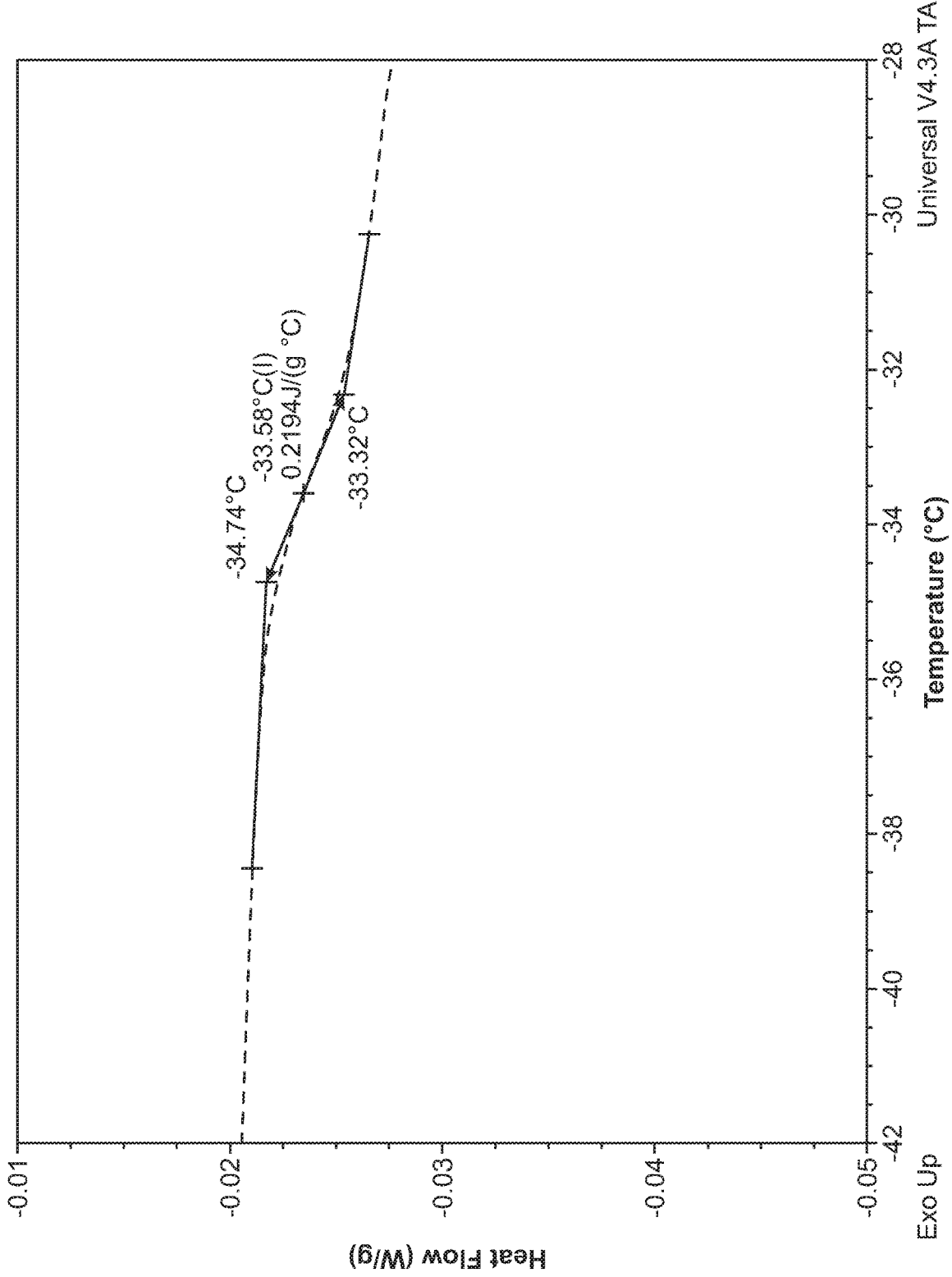
FIG. 2A shows a Differential Scanning calorimetry (DSC) thermogram of a 5% sucrose formulation with a serum sample
Figure 2B:
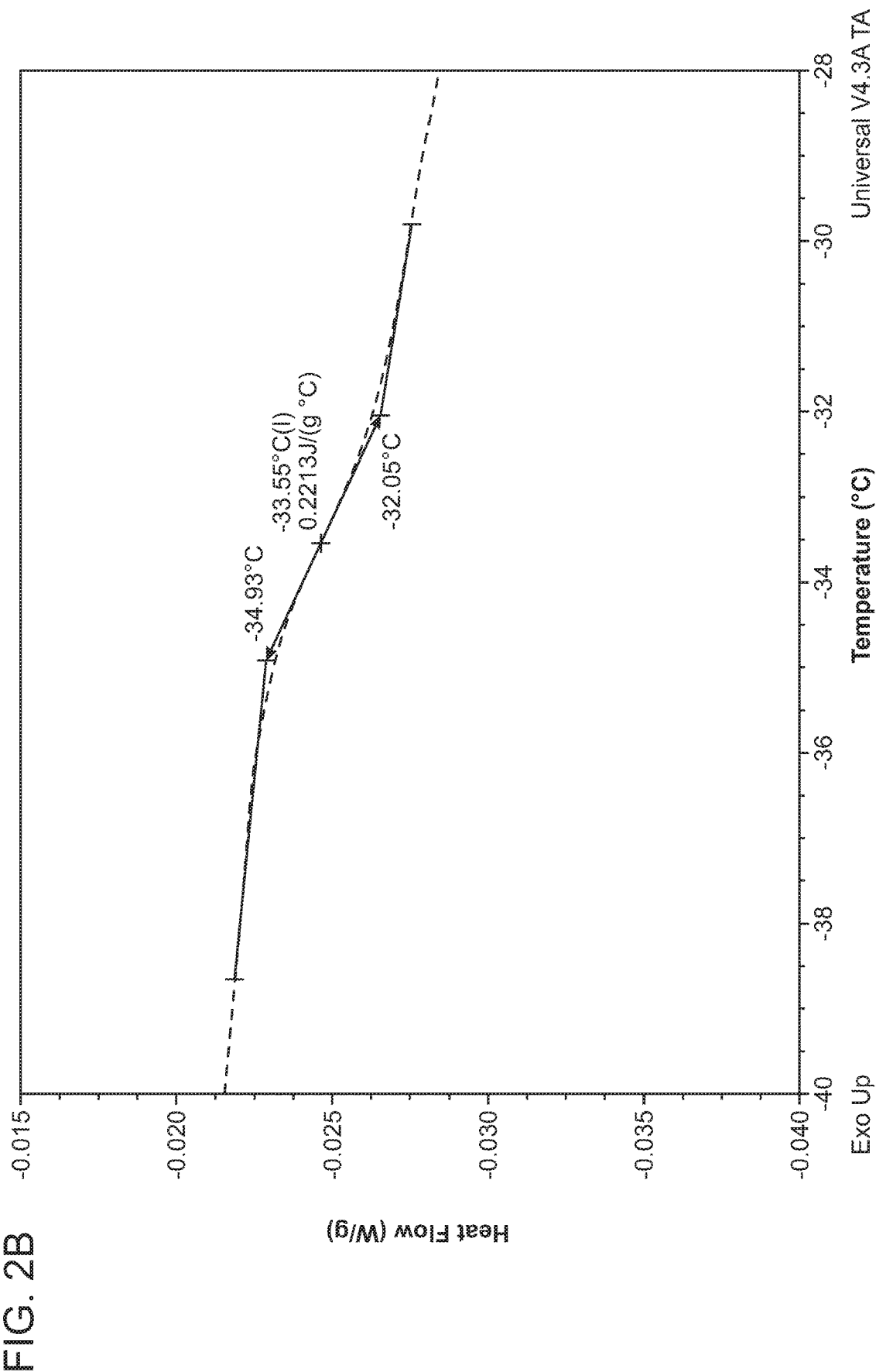
FIG. 2B shows a Differential Scanning calorimetry (DSC) thermogram of a 5% sucrose formulation with a plasma sample

The formulation containing serum was mixed thoroughly for 15 seconds with pipet before 10 µL was added to Al pans carefully. At a temperature of about −35° C., a baseline shift in the heat flow, characteristic of the glass transition, was observed and an average glass transition temperature of −33.5° C. was obtained during the ramp up (FIG. 2A). The formulation containing plasma was mixed thoroughly for 15 seconds with pipet before 10 µL was added to Al pans carefully. At a temperature of about −35° C., a baseline shift in the heat flow, characteristic of the glass transition, was observed and an average glass transition temperature of −33.5° C. was obtained during the ramp up (FIG. 2B).

A formulation of 5% sucrose with serum at −25° C., a collapse front, which indicates a loss of structural integrity, began to appear and the sublimation front eventually collapsed at −23° C. A formulation of 5% sucrose with plasma at −23° C., a collapse front, which indicates a loss of structural integrity, began to appear, and the sublimation front eventually collapsed at −21° C.

The glass transition temperature (Tg') for sucrose formulation containing serum and plasma were measured using standard DSC and were observed to be in between −35° C. to −32° C. range. The structural changes in FDM were prominent with a visible sublimation and a classical collapse which occurred at −24° C. for the formulation containing serum and −22° C. for the formulation containing plasma.

The disclosure has been described herein by reference to certain embodiments. However, as other variations will become apparent to those skilled in the art, the disclosure is not to be considered as limited thereto. Any compositions or methods provided herein can be combined with one or more of any of the other compositions and methods provided herein. Other features and advantages of the compositions and methods described herein will be apparent to those skilled in the art from the detailed description and claims. All patents, patent applications, and references cited anywhere are hereby incorporated by reference in their entirety.

Those skilled in the art will recognize, or be able to ascertain using no more than routine experimentation, many equivalents to the specific embodiments described herein. Such equivalents are intended to be encompassed by the following claims.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A freeze-dried composition comprising allogenic serum or umbilical cord serum, and a polysaccharide or derivative thereof having a molecular weight of 100 to 1200 kDA, wherein the composition comprises 50-90 weight percent (wt%) serum and 10-40 wt % polysaccharide based on the total dry weight of the composition, and wherein the polysaccharide is hydrophobically modified chitosan.

2. The freeze-dried composition according to claim 1, the comprising umbilical cord serum.

3. The freeze-dried composition according to claim 1, further comprising an additive.

4. The freeze-dried composition according to claim 3, wherein the additive is selected from the group consisting of: chitosan, alginate, gelatin, hyaluronic acid, gellan gum, dextran, polyethylene glycol, polyethylene oxide, glucose, glucosamine, sodium chloride, polylactic acid, polylactic-co-glycolic acid, and glycerol.

5. The freeze-dried composition of claim 1, wherein the composition is an ophthalmic composition.

6. The freeze-dried composition of claim 1, in the form of a cohesive solid material having a defined shape, wherein the defined shape is a disc, a wafer, a lens, a pessary, a wound dressing, or a denture.

7. The freeze-dried composition of claim 1, in the form of dry powder.

8. A pharmaceutical composition comprising the composition of claim 1, and a carrier.

9. A method for treating dry eye syndrome in a subject in need thereof, the method comprising administering the freeze-dried composition of claim 1 to the subject wherein the serum is present in the composition in an amount effective to treat dry eye syndrome in the eye of the subject.

10. A method for treating a non-keratinized epithelial surface of a subject in need of such treatment, the method comprising applying the freeze-dried composition of claim 1 to the non-keratinized epithelial surface wherein the serum is present in the composition in an amount effective to treat the non-keratinized epithelial surface of the subject.

11. A method for treating dry eye syndrome in a subject in need thereof, the method comprising reconstituting the freeze-dried composition of claim 1 in an aqueous solvent to provide a composition of pH 7-7.4 in which the hydrophobically modified chitosan is present at a concentration of from 0.025% to 2.0%, and topically administering the composition to an eye of the subject.

12. A method for treating a non-keratinized epithelial surface of a subject in need of such treatment, the method comprising reconstituting the freeze-dried composition of claim 1 in an aqueous solvent to provide a composition of pH 7-7.4 in which the hydrophobically modified chitosan is present at a concentration of from 0.025% to 2.0%, and topically administering the composition to the non-keratinized epithelial surface of the subject.

13. The method of claim 11 or 12, wherein the composition is formulated as a solution, suspension, emulsion, gel, or ointment.

14. The method of claim 13, wherein the composition comprises one or more additives selected from glycine, ascorbic acid, alginate, or gelatin.

15. The method of claim 13, wherein the composition is sterile.

* * * * *